(12) United States Patent
Wickham et al.

(10) Patent No.: US 6,329,190 B1
(45) Date of Patent: *Dec. 11, 2001

(54) TARGETTING ADENOVIRUS WITH USE OF CONSTRAINED PEPTIDE MOTIFS

(75) Inventors: Thomas J. Wickham, Potomac; Petrus W. Roelvink, Olney; Imre Kovesdi, Rockville, all of MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/455,061

(22) Filed: Dec. 6, 1999

Related U.S. Application Data

(63) Continuation of application No. 09/130,225, filed on Aug. 6, 1998, now Pat. No. 6,057,155, which is a division of application No. 08/701,124, filed on Aug. 21, 1996, now Pat. No. 5,846,782, which is a continuation-in-part of application No. 08/563,368, filed on Nov. 28, 1995, now Pat. No. 5,965,541.

(51) Int. Cl.[7] .......................... C07K 14/075; C12N 5/16; C12N 15/861; C07H 21/04

(52) U.S. Cl. .................. 435/235.1; 435/325; 435/320.1; 435/91.4; 435/456; 435/375; 435/69.7; 530/350; 536/23.1; 536/23.4

(58) Field of Search .............................. 530/350; 435/71, 435/5, 69.1, 69.7, 91.4, 456, 325, 375, 320.1, 235.1; 536/23.1, 23.4

(56) References Cited

U.S. PATENT DOCUMENTS

| | | | |
|---|---|---|---|
| 4,487,829 | 12/1984 | Sharp et al. | 435/5 |
| 4,517,686 | 5/1985 | Ruoslahti et al. | 623/1.49 |
| 4,578,079 | 3/1986 | Ruoslahti et al. | 623/23.76 |

(List continued on next page.)

FOREIGN PATENT DOCUMENTS

| | | |
|---|---|---|
| 259212 | 3/1988 | (EP) . |
| 2-078631 | 3/1990 | (JP) . |
| WO 88/05077 | 7/1988 | (WO) . |
| WO 90/12087 | 10/1990 | (WO) . |
| WO 91/00360 | 1/1991 | (WO) . |
| WO 91/05805 | 5/1991 | (WO) . |
| WO 91/05871 | 5/1991 | (WO) . |
| WO 92/02553 | 2/1992 | (WO) . |
| WO 92/06180 | 4/1992 | (WO) . |
| WO 92/13081 | 8/1992 | (WO) . |

(List continued on next page.)

OTHER PUBLICATIONS

Berendsen, H.C. A Glimpse of the Holy Grail? Science. vol. 282, pp. 642–643, 1998.*
Albiges–Rizo et al., *Journal of Biological Chemistry*, 266(6), 3961–3967 (1991).
Athapilly et al., *J. Mol. Biol.*, 242, 430–455 (1994).

(List continued on next page.)

*Primary Examiner*—David Guzo
*Assistant Examiner*—Gerald G. Leffers, Jr.
(74) *Attorney, Agent, or Firm*—Leydig, Voit & Mayer, Ltd.

(57) ABSTRACT

The present invention provides a chimeric adenovirus fiber protein, which differs from the wild-type coat protein by the introduction of a nonnative amino acid sequence in a conformationally-restrained manner. Such a chimeric adenovirus fiber protein according to the invention is able to direct entry into cells of a vector comprising the chimeric fiber protein that is more efficient than entry into cells of a vector that is identical except for comprising a wild-type adenovirus fiber protein rather than the chimeric adenovirus fiber protein. The nonnative amino acid sequences encodes a peptide motif that comprises an epitope for an antibody, or a ligand for a cell surface receptor, that can be employed in cell targeting. The present invention also pertains to vectors comprising such a chimeric adenovirus fiber protein, and to methods of using such vectors.

20 Claims, 17 Drawing Sheets

U.S. PATENT DOCUMENTS

| | | | |
|---|---|---|---|
| 4,589,881 | 5/1986 | Pierschbacher et al. | 623/23.76 |
| 4,593,002 | 6/1986 | Dulbecco | 435/91.41 |
| 4,792,525 | 12/1988 | Ruoslahti et al. | 435/402 |
| 4,797,368 | 1/1989 | Carter et al. | 435/320.1 |
| 4,956,281 | 9/1990 | Wallner | 435/69.3 |
| 5,024,939 | 6/1991 | Gorman | 435/69.1 |
| 5,096,815 | 3/1992 | Wu et al. | 435/69.1 |
| 5,166,320 | 11/1992 | Wu et al. | 530/395 |
| 5,198,346 | 3/1993 | Ladner et al. | 435/69.1 |
| 5,204,445 | 4/1993 | Plow et al. | 530/326 |
| 5,223,394 | 6/1993 | Wallner | 435/6 |
| 5,223,409 | 6/1993 | Ladner et al. | 435/69.7 |
| 5,240,846 | 8/1993 | Collins et al. | 435/371 |
| 5,246,921 | 9/1993 | Reddy et al. | 514/44 |
| 5,332,567 | 7/1994 | Goldenberg | 424/1.49 |
| 5,349,053 | 9/1994 | Landolfi | 530/351 |
| 5,403,484 | 4/1995 | Ladner et al. | 435/235.1 |
| 5,436,146 | 7/1995 | Shenk et al. | 435/457 |
| 5,443,953 | 8/1995 | Hansen et al. | 424/1.49 |
| 5,474,935 | 12/1995 | Chatterjee et al. | 435/320.1 |
| 5,521,291 | 5/1996 | Curiel et al. | 530/391.7 |
| 5,534,423 | 7/1996 | Palsson et al. | 435/456 |
| 5,543,328 | 8/1996 | McClelland et al. | 435/320.1 |
| 5,547,932 | 8/1996 | Curiel et al. | 435/456 |
| 5,552,311 | 9/1996 | Sorscher et al. | 435/348 |
| 5,559,099 | 9/1996 | Wickham et al. | 514/44 |
| 5,571,698 | 11/1996 | Lardner et al. | 435/69.7 |
| 5,661,133 | 8/1997 | Leiden et al. | 514/44 |
| 5,672,344 | 9/1997 | Kelley et al. | 424/93.2 |
| 5,674,722 | 10/1997 | Mulligan et al. | 435/456 |
| 5,695,991 | 12/1997 | Lindholm et al. | 435/320.1 |
| 5,846,782 * | 12/1998 | Wickham et al. | 435/697 |
| 6,057,155 * | 12/1998 | Wickham et al. | 435/325 |

FOREIGN PATENT DOCUMENTS

| | | |
|---|---|---|
| WO 93/03769 | 3/1993 | (WO) . |
| WO 93/06223 | 4/1993 | (WO) . |
| WO 93/07282 | 4/1993 | (WO) . |
| WO 93/07283 | 4/1993 | (WO) . |
| WO 93/25234 | 12/1993 | (WO) . |
| WO 94/06920 | 3/1994 | (WO) . |
| WO 94/08026 | 4/1994 | (WO) . |
| WO 94/10323 | 5/1994 | (WO) . |
| WO 94/11506 | 5/1994 | (WO) . |
| WO 94/15644 | 7/1994 | (WO) . |
| WO 94/17832 | 8/1994 | (WO) . |
| WO 94/24299 | 10/1994 | (WO) . |
| WO 94/26915 | 11/1994 | (WO) . |
| WO 95/05201 | 2/1995 | (WO) . |
| WO 95/06745 | 3/1995 | (WO) . |
| WO 95/14785 | 6/1995 | (WO) . |
| WO 95/16037 | 6/1995 | (WO) . |
| WO 95/21259 | 8/1995 | (WO) . |
| WO 95/26412 | 10/1995 | (WO) . |
| WO 95/27071 | 10/1995 | (WO) . |
| WO 95/31187 | 11/1995 | (WO) . |
| WO 95/31566 | 11/1995 | (WO) . |
| WO 96/00790 | 1/1996 | (WO) . |
| WO 96/07734 | 3/1996 | (WO) . |
| WO 96/07739 | 3/1996 | (WO) . |
| WO 96/10087 | 4/1996 | (WO) . |
| WO 96/13597 | 5/1996 | (WO) . |
| WO 96/14837 | 5/1996 | (WO) . |
| WO 96/17073 | 6/1996 | (WO) . |
| WO 96/18740 | 6/1996 | (WO) . |
| WO 96/26281 | 8/1996 | (WO) . |
| WO 97/20051 | 6/1997 | (WO) . |
| WO 98/11221 | 3/1998 | (WO) . |
| WO 98/13499 | 4/1998 | (WO) . |
| WO 98/22609 | 5/1998 | (WO) . |
| WO 98/32842 | 7/1998 | (WO) . |

OTHER PUBLICATIONS

Aumailley et al., *FEBS*, 291, 50–54 (1991).
Bai et al., *J. Virol.*, 67(9), 5198–5205 (1993).
Ball–Goodrich et al., *Virology*, 184, 175–186 (1991).
Barinaga, *Science*, 266, 1326 (1994).
Batra et al., *Gene Therapy*, 1, 255–260 (1994).
Boursnell et al., *Gene*, 13, 311–317 (1981).
Caillet–Boudin et al., *J. Mol. Biol.*, 217, 477–486 (1991).
Chroboczek et al., *Virology*, 186, 280–285 (1992).
Chu et al., *Gene Therapy*, 1, 292–299 (1994).
Cotten et al., *Proc. Natl. Acad. Sci. USA*, 89, 6094–6098 (1992).
Cotten et al., *Proc. Natl. Acad. Sci.*, 87, 4033–4037 (1990).
Crawford–Miksza et al., *Journal of Virology*, 70(3), 1836–1844 (1996).
Crompton et al., *J. Gen. Virol.*, 75(1), 133–139 (1994).
Crystal, *Science*, 270, 404–410 (1995).
Curiel et al., *Human Gene Therapy*, 3, 147–154 (1992).
Curiel et al., *Proc. Natl. Acad. Sci. USA*, 88, 8850–8854 (1991).
Database WPI, Week 9017, Derwent Publications Ltd., AN 90–129060/17 (JP 2,078,631 Abstract).
Database WPI, Week 9316, Derwent Publications Ltd., AN 93–134470/16 (WO 93/07283 English Abstract).
Database WPI, Week 9440, Derwent Publications Ltd., AN 94–317775/40 (WO 94/24299 English Abstract).
Defer et al., *Journal of Virology*, 64(8), 3661–3673 (1990).
Dupuit et al., *Human Gene Therapy*, 6, 1185–1193 (1950).
Etienne–Julan et al., *Journal of General Virology*, 73, 3251–3255 (1992).
Falck–Pedersen, Abstract of National Institutes of Health Grant Application No. 1 PO1 HL51746–01UB: 0004 entitled "Gene Therapy for Cystic Fibrosis" (1994).
Falgout et al., *Journal of Virology*, 62(2), 622–625 (1988).
Gall et al., *Journal of Virology*, 70, 2116–2123 (1996).
Greber et al., *Cell*, 75, 477–486 (1993).
Green et al., *EMBO Journal*, 2(8), 1357–1365 (1983).
Grubb et al., *Nature*, 371, 802–806 (1994).
Han et al., *Proc. Natl. Acad. Sci. USA*, 92, 9747–9751 (1995).
Henry et al., *Journal of Virology*, 68(8), 5239–5246 (1994).
Hong et al., *Virology*, 185, 758–767 (1991).
Horvath et al., *Journal of Virology*, 62(1), 341–345 (1988).
Huang et al., *Journal of Virology*, 69(4), 2257–2263 (1995).
Jolly, *Cancer Gene Therapy*, 1(1), 51–64 (1994).
Karyan et al., *Virology*, 202, 782–785 (1994).
Kass–Eisler et al., *Proc. Natl Acad. Sci. USA*, 90, 11498–11502 (1993).
Kinloch et al., *J. Biol. Chem.*, 259, 6431–6436 (1984).
Koivunen et al., *Bio/Technology*, 13, 265–269 (1995).
Komoriya et al., *Journal of Biological Chemistry*, 266(23), 15075–15079 (1991).
Legrand et al., *Cold Spring Harbor Meeting on Gene Therapy*, 184 (1996).
Maraveyas et al., *Acta Oncologica*, 32(7/8), 741–746 (1993).
Marshall, *Science*, 269, 1050–1055 (1995).
Massia et al., *J. Biolog. Chem.*, 11, 8053–8059 (1993).
Mastrangeli et al., *Human Gene Therapy*, 7, 79–87 (1996).
Mastrangeli et al., *Ped. Pulm., Suppl.*, 12, 230, Abst. No. 180 (1995).

Mathais et al., *J. Virol.*, 68 (10) 6811–6814 (1994).
Mathias et al., *J. Virol.*, 68, 6811–6814 (1994).
Michael et al., *Gene Therapy*, 2, 660–668 (1995).
Michael et al., *J. Biolog. Chem.*, 268(10), 6866–6869 (1993).
Michael et al., presented at Adenovirus Workshop: St. Andrews University, p. 52 (Jul. 13–15, 1995).
Miller et al., *FASEB J.*, 9, 190–199 (1995).
Neda et al., *Journal of Biological Chemistry*, 266(22), 14143–14146 (1991).
Nemerow et al., *In Biology of Vitronectins and Their Receptors*, Preissner et al., eds., 177–184 (Elsevier Science Publishers, 1993).
Nemerow et al., *Trends in Cell Biology*, 4, 52–55 (1994).
Novelli et al., *Virology*, 185, 365–376 (1991).
Orkin et al., *Report and Recommendations of the Panel to Assess the NIH Investment in Research on Gene Therapy*, (1995).
Peteranderl et al., *Biochemistry*, 31, 12272–12276 (1992).
Roberts et al., *Science*, 232, 1148–1151 (1986).
Russell et al., *Nature Medicine*, 2, 276–277 (1996).
Russell et al., *Nucleic Acids Research*, 21(5), 1081–1085 (1993).

Signas et al., *J. Virol.*, 53(2), 672–678 (1985).
Silver et al., *Virology*, 165, 377–387 (1988).
Stewart et al., *EMBO J.*, 12, 2589–2599 (1993).
Toogood et al., *J. Gen. Virol.*, 73, 1429–1435 (1992).
Von Seegern et al., *Cold Spring Harbor Meeting on Gene Therapy*, 312 (1996).
Wagner et al., *Proc. Natl. Acad. Sci. USA*, 89, 6099–6103 (1992).
Watkins et al., presented at *Keystone Symposium on Molecular and Cellular Biology*, Abst. No. 336 (Taos: NM, Feb. 22–28, 1996).
Watson et al., *J. Virol.*, 69, 525–535 (1988).
Watson et al., *Journal of Virology*, 69, 525–535 (1988).
Wickham et al., *Cell*, 73, 309–319 (1993).
Wickham et al., *Gene Therapy*, 2, 750–756 (1995).
Wickham et al., *J. Cell Biol.*, 127, 257–264 (1994).
Wickham et al., *Journal of Virology*, 70, 6831–6838 (1996).
Xia et al., *Structure*, 2, 1259–1270 (1994).

* cited by examiner

SpeI
ATTACACTTAATGGCACTAGTGAATCCACAGAAACT [SEQ ID NO:73]
▶ IleThrLeuAsnGlyThrSerGluSerThrGluThr [SEQ ID NO:74]

```
                               SpeI
ATTACACTTAATGGCACTAGAAAAGAAAACGCAAAAGAAGAAGAAGACTAGTGAATCCACAGAAACT    [SEQ ID NO:26]
▲IleThrLeuAsnGlyThrArgLysLysLysArgLysLysLysThrSerGluSerThrGluThr       [SEQ ID NO:27]
```

SpeI

ATTACACTTAATGGCACTAGAGAGACTACAAGGACGACGATGATAAGACTAGTGAATCCACAGAAACT [SEQ ID NO:28]
▲IleThrLeuAsnGlyThrArgAspTyrLysAspAspAspAspLysThrSerGluSerThrGluThr [SEQ ID NO:29]

BamHI
GCCCAAGAAGGATCAGATCAGGTTCAGGGAGTGGCTCTGCCTGACTGTCGGGGCCGATTGTTTTGCGGTTAAGGATCCAATAA  [SEQ ID NO:48]
AlaGlnGluGlySerGlySerGlySerGlySerAlaCysAspCysArgGlyAspCysPheCysGly  [SEQ ID NO:49]

BamHI SpeI
[SEQ ID NO:75] GCCCAAGAAGGATCCGGTTCAGGATCTGGCAGTGGCTCGACTAGTGAAATTCTTGACGTCGGAGAGATCCTCGAGCTCGGGGAAATACTGACGCTCTAGTTAA
[SEQ ID NO:76] AlaGlnGluGlySerGlySerGlySerGlySerGlySerThrSerGluIleLeuAspValGlyGluIleLeuGluLeuGlyGluIleLeuThrLeu***

BamHI                                                                                           SpeI
[SEQ ID NO:77]  GCCCAAGAAGGATCCGGTTCAGGATCTGGCAGTGGCTCGACTAGTGGATACATTGGGTCCCGAGGATATATAGGCTCAAGATCTAGTTAA
[SEQ ID NO:78]  AlaGlnGluGlySerGlySerGlySerGlyGlySerThrSerGlySerArgGlyTyrIleGlySerArgGlyTyrIleGlySerArgSer

TARGETTING ADENOVIRUS WITH USE OF CONSTRAINED PEPTIDE MOTIFS

RELATED APPLICATIONS

This is continuation application of U.S. patent application Ser. No. 09/130,225, filed Aug. 6, 1998, now U.S. Pat. No. 6,057,155, which is a divisional application of U.S. patent application Ser. No. 08/701,124, filed Aug. 21, 1996, now U.S. Pat. No. 5,846,782, which is a continuation-in-part application of U.S. patent application Ser. No. 08/563,368, filed Nov. 28, 1995, now U.S. Pat. No. 5,965,541.

TECHNICAL FIELD OF THE INVENTION

The present invention pertains to a chimeric adenovirus fiber protein comprising a constrained nonnative amino acid sequence.

BACKGROUND OF THE INVENTION

Despite their prior poor reputation as major pathogenic agents that lead to numerous infectious diseases, adenoviruses (and particularly, replication-deficient adenoviruses) have more recently attracted considerable recognition as highly effective viral vectors for gene therapy. Adenoviral vectors offer exciting possibilities in this new realm of therapeutics based on their high efficiency of gene transfer, substantial carrying capacity, and ability to infect a wide range of cell types (Crystal, *Science,* 270, 404–410 (1995); Curiel et al., *Human Gene Therapy,* 3, 147–154 (1992); International Patent Application WO 95/21259).

Due to these desirable properties of adenoviruses, recombinant adenoviral vectors have been used for the cell-targeted transfer of one or more recombinant genes to diseased cells or tissue in need of treatment. In terms of the general structure of an adenovirus, under the electron microscope, an adenovirus particle resembles a space capsule having protruding antennae (Xia et al., *Structure,* 2, 1259–1270 (1994)). The viral capsid comprises at least six different polypeptides, including 240 copies of the trimeric hexon (i.e., polypeptide II) and 12 copies each of the pentameric penton (polypeptide III) base and trimeric fiber (Xia et al., supra).

An adenovirus uses two separate cellular receptors, both of which must be present, to attach to and infect a cell (Wickham et al., *Cell,* 73, 309–319 (1993)). First, the adenovirus fiber protein attaches the virus to a cell by binding to an as yet unidentified receptor. Then, the penton base binds to $\alpha_v$ integrins, which are a family of heterodimeric cell-surface receptors that mediate cellular adhesion to the extracellular matrix molecules, as well as other molecules (Hynes, *Cell,* 69, 11–25 (1992)). Once an adenovirus is attached to a cell, it undergoes receptor-mediated internalization into clathrin-coated endocytic vesicles and is stepwise stripped down to the viral double-stranded genome, and then the genome (and some accompanying viral components) subsequently is transported to the cell nucleus, thus initiating infection (Svennson et al., *J. Virol.,* 51, 687–694 (1984); Chardonnet et al., *Virology,* 40, 462–477 (1970); Greber et al., *Cell,* 75, 477–486 (1993); Fitzgerald et al., *Cell,* 32, 607–617 (1983)).

The fiber monomer consists of an amino terminal tail (which attaches noncovalently to the penton base), a shaft (whose length varies among different virus serotypes), and a carboxy terminal globular knob domain (which is necessary and sufficient for host cell binding) (Devaux et al., *J. Molec. Biol.,* 215, 567–588 (1990); Xia et al., supra; Green et al., *EMBO J.,* 2, 1357–1365 (1983); Henry et al., *J. Virology,* 68(8), 5239–5246 (1994)). The regions necessary for trimerization of fiber (which is required for penton base binding) also are located in the knob region of the protein (Henry et al. (1994), supra; Novelli et al., *Virology,* 185, 365–376 (1991)). The fiber, together with the hexon, determine the serotype specificity of the virus, and also comprise the main antigenic determinants of the virus (Watson et al., *J. Gen. Virol.,* 69, 525–535 (1988)).

This ability of adenoviral fiber and hexon protein to act as targets for a host immune response initially hampered attempts at adenoviral-mediated gene therapy. Namely, alterations in gene expression mediated by adenovirus are not permanent since the vector is not stably maintained. However, following adenoviral vector re-administration to prolong the therapeutic response, neutralizing antibodies can be raised against the adenoviral fiber and/or hexon proteins, thus circumventing protein production (Wohlfart, *J. Virology,* 62, 2321–2328 (1988); Wohlfart et al., *J. Virology,* 56, 896–903 (1985)). Fortunately, such an immune response will not be generated with all uses of adenoviral vectors. Similarly, it is now known that if the presence of such neutralizing antibodies impedes adenoviral-mediated intracellular delivery, another adenoviral vector, e.g., another serotype adenoviral vector, or another adenovirus vector lacking the epitope against which the antibody is directed, can be employed instead (Crompton et al., *J. Gen. Virol.,* 75, 133–139 (1994)). Moreover, newer and effective techniques are constantly emerging to prevent an antibody response against the virus from precluding effective re-administration of an adenoviral vector (see, e.g., International Patent Application WO 96/12406; Mastrangeli et al., *Human Gene Therapy,* 7, 79–87 (1996)).

Thus, adenoviral-mediated gene therapy continues to hold great promise, in particular, with respect to redirecting adenovirus tropism. Namely, even though adenovirus can enter an impressive variety of cell types (see, e.g., Rosenfeld et al., *Cell,* 68, 143–155 (1992); Quantin et al., *Proc. Natl. Acad. Sci.,* 89, 2581–2584 (1992)); Lemarchand et al, *Proc. Natl. Acad. Sci.,* 89, 6482–6486 (1992); Anton et al., *J. Virol.,* 69, 4600–4606 (1995); LaSalle et al., *Science,* 259, 988–990 (1993)), there still appear to be cells (e.g., lymphocytes) which are not readily amenable to adenovirus-mediated gene delivery (see, e.g., Grubb et al., *Nature,* 371, 802–806 (1994); Dupuit et al., *Human Gene Therapy,* 6, 1185–1193 (1995); Silver et al., *Virology* 165, 377–387 (1988); Horvath et al., *J. Virol.,* 62(1), 341–345 (1988)). Similarly, even when targeting to cells that readily are infected by adenovirus, in many cases, very high levels of adenovirus particles have been used to achieve transduction. This is disadvantageous inasmuch as any immune response associated with adenoviral infection necessarily would be exacerbated with such high levels.

Accordingly, researchers are seeking new ways to selectively introduce adenoviruses into cells that cannot be infected by adenoviruses, and to increase the effectiveness of adenoviral delivery into cells that are infected by adenoviruses. The general principle of redirecting adenovirus tropism is straightforward. In one common approach, by incorporating peptide binding motifs into an adenovirus coat protein such as fiber protein, the virus can be redirected to bind a cell surface binding site that it normally does not bind (see, e.g., Michael et al., *Gene Therapy,* 2, 660–668 (1995); International Patent Application WO 95/26412; International Patent Application WO 94/10323; International Patent Application WO 95/05201). A peptide binding motif is a short sequence of amino acids such as an epitope for an antibody (e.g., a bispecific antibody), or a ligand for a cell surface binding site (e.g., a receptor), that can be employed in cell targeting. When the peptide motif binds, for instance to its corresponding cell surface binding site to which adenovirus normally does not bind, or binds with only low affinity, the adenovirus carrying the peptide motif then can selectively deliver genes to the cell comprising this binding site in a specific and/or more efficient manner.

However, simply incorporating a known peptide motif into the fiber protein of an adenovirus may not be enough to allow the virus to bind and effectively transduce a target cell. The effectiveness of the peptide motif in redirecting virus binding to a new cell surface binding site depends on multiple factors, including the availability of the peptide motif to bind to the cell surface receptor, the affinity of the peptide motif for the cell surface binding site, and the number of target binding sites (e.g., receptors) present on the cell targeted for gene delivery. While the lattermost factor currently cannot be manipulated, in in vivo applications, the former two would appear to present areas for improvement of prevailing adenoviral-mediated gene therapy. For instance, earlier researchers have not considered that if the peptide motif is buried within the structure of the fiber protein, and/or masked by the surrounding structure of the protein, the peptide motif will not be able to interact with and bind its target. Similarly, previous researchers have not addressed that it is the affinity of the peptide motif for the cell surface binding site (e.g., receptor) which determines how efficiently the virus can initiate and maintain a binding contact with the target receptor, resulting in cell infection/transduction.

Thus, there remains a need for improved methods of cell targeting, and adenoviral vectors by which this can be accomplished. The present invention seeks to overcome at least some of the aforesaid problems of recombinant adenoviral gene therapy. In particular, it is an object of the present invention to provide improved vectors and methods for cell targeting through provision of a chimeric adenovirus fiber protein comprising a constrained peptide motif. These and other objects and advantages of the present invention, as well as additional inventive features, will be apparent from the following detailed description.

BRIEF SUMMARY OF THE INVENTION

The present invention provides a chimeric adenoviral fiber protein which differs from the wild-type (i.e., native) fiber protein by the introduction of a nonnative amino acid sequence in a conformationally-restrained (i.e., constrained) manner. The introduction results in the insertion of, or creation of, a constrained peptide motif that confers upon the resultant chimeric adenovirus fiber protein an ability to direct entry into cells of a vector comprising the chimeric fiber protein that is more efficient than entry into cells of a vector that is identical except for comprising a wild-type adenovirus fiber protein, and/or an ability to direct entry into cells that adenovirus comprising the wild-type fiber protein typically does not infect/transduce. The present invention also provides vectors that comprise the chimeric adenovirus fiber protein, and methods of constructing and using such vectors.

DETAILED DESCRIPTION OF THE INVENTION

Figure 1:
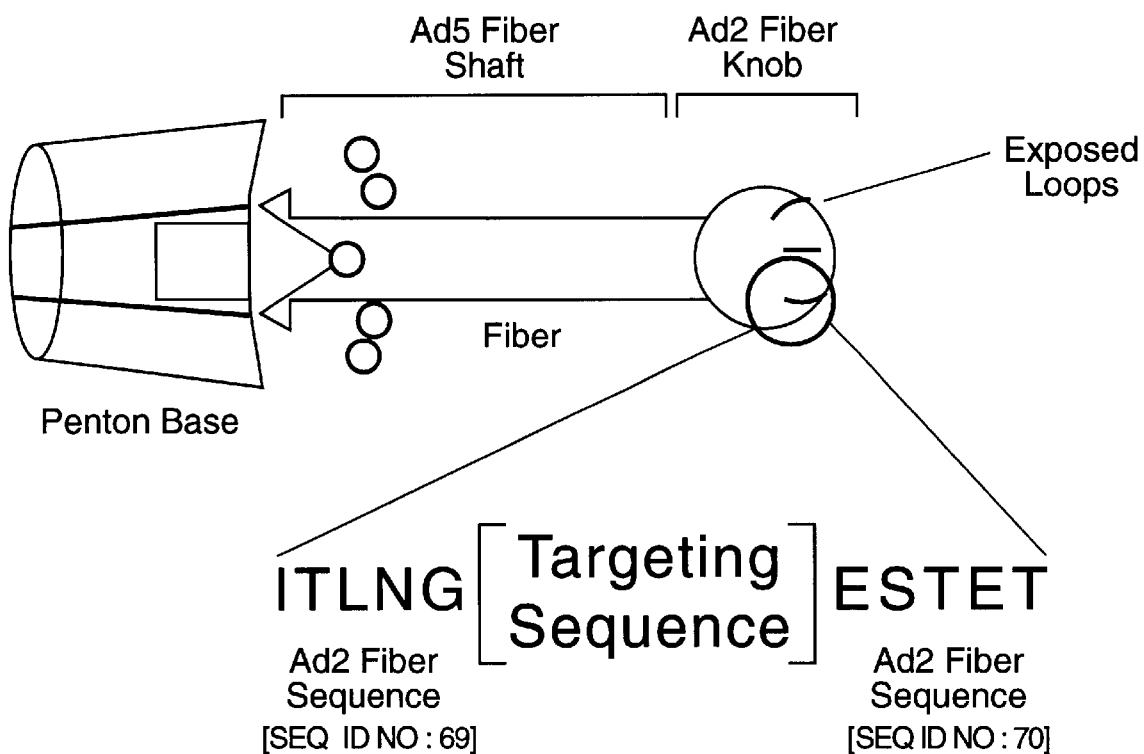
FIG. 1 is a diagram that illustrates the method of the invention of targeting adenovirus by conformationally restraining a nonnative amino acid sequence in an exposed loop of the fiber knob to comprise a peptide binding motif.

The present invention provides, among other things, a recombinant adenovirus comprising a chimeric fiber protein. The chimeric fiber protein comprises a constrained nonnative amino acid sequence, in addition to, or in place of, a native amino acid sequence. This nonnative amino acid sequence allows the chimeric fiber (or a vector comprising the chimeric fiber) to more efficiently bind to and enter cells.

Chimeric Adenovirus Fiber Protein

A "fiber protein" according to the invention preferably comprises an adenoviral fiber protein. Any one of the serotypes of human or nonhuman adenovirus (as described later in the context of the vector comprising a chimeric fiber protein) can be used as the source of the fiber protein or fiber gene. Optimally, however, the adenovirus is an Ad2 or Ad5 adenovirus.

The fiber protein is "chimeric" in that it comprises amino acid residues that are not typically found in the protein as isolated from wild-type adenovirus (i.e., comprising the native protein, or wild-type protein). The fiber protein thus comprises a "nonnative amino acid sequence". By "nonnative amino acid sequence" is meant a sequence of any suitable length, preferably from about 3 to about 200 amino acids, optimally from about 3 to about 30 amino acids. Desirably, the nonnative amino acid sequence is introduced into the fiber protein at the level of gene expression (i.e., by introduction of a "nucleic acid sequence that encodes a nonnative amino acid sequence"). Such a nonnative amino acid sequence either is introduced in place of adenoviral sequences, or in addition to adenoviral sequences. Regardless of the nature of the introduction, its integration into an adenoviral fiber protein at the level of either DNA or protein, results in the generation of a peptide motif (i.e., a peptide binding motif) in the resultant chimeric fiber protein.

The peptide motif allows for cell targeting, for instance, by comprising an epitope for an antibody, or a ligand for a cell surface binding site. The peptide motif optionally can comprise other elements of use in cell targeting (e.g., a single-chain antibody sequence). The peptide binding motif may be generated by the insertion, and may comprise, for instance, native and nonnative sequences, or may be entirely made up of nonnative sequences. The peptide motif that results from the insertion of the nonnative amino acid sequence into the chimeric fiber protein can be either a high affinity peptide (i.e., one that binds its cognate binding site when provided at a relatively low concentration) or a low affinity peptide (i.e., one that binds its cognate binding site when provided at a relatively high concentration). Preferably, however, the resultant peptide motif is a high affinity motif, particularly one that has become of high affinity for its cognate binding site due to its constraint within the adenovirus fiber protein.

An "antibody" includes, but is not limited to, immunoglobulin molecules and immunologically active portions of immunoglobulin molecules such as portions containing a paratope (i.e., an antigen binding site). In particular, an antibody preferably can be a bispecific antibody, i.e., having one paratope directed to an epitope of the chimeric fiber protein, and another paratope directed to an epitope of a cell surface binding site.

A "cell surface binding site" encompasses a receptor (which preferably is a protein, carbohydrate, glycoprotein, or proteoglycan) as well as any oppositely charged molecule (i.e., oppositely charged with respect to the chimeric coat protein) or other type of molecule with which the chimeric coat protein can interact to bind the cell, and thereby promote cell entry. Examples of potential cell surface binding sites include, but are not limited to: heparin and chondroitin sulfate moieties found on glycosaminoglycans; sialic acid moieties found on mucins, glycoproteins, and gangliosides; major histocompatibility complex I (MHC I) glycoproteins; common carbohydrate components found in membrane glycoproteins, including mannose, N-acetylgalactosamine, N-acetyl-glucosamine, fucose, galactose, and the like. However, a chimeric fiber protein according to the invention, and methods of use thereof, is not limited to any particular mechanism of cellular interaction (i.e., interaction with a particular cell surface binding site) and is not to be so construed.

A cell surface binding site according to the invention preferably is one that previously was inaccessible to interaction with a wild-type adenoviral fiber protein, or was accessible only at a very low level, as reflected by the reduced efficiency of entry of a wild-type adenoviral fiber protein-containing vector as compared with a vector comprising a chimeric adenovirus fiber protein according to the invention. The insertion of the nonnative amino acid sequence in the chimeric fiber protein thus desirably imparts upon the chimeric fiber protein an ability to bind to a binding site present on a cell surface which wild-type fiber protein does not bind, or binds with very low affinity. This preferably results in a situation wherein the chimeric adenovirus fiber protein is able to direct entry into cells of a vector via the interaction of the nonnative amino acid sequence, either directly or indirectly, with a cellular receptor other than the fiber receptor.

This also preferably results in a situation wherein the chimeric adenovirus fiber protein is able to direct entry into cells of a vector comprising the chimeric adenovirus fiber that is more efficient than entry into cells of a vector that is identical except for comprising a wild-type adenovirus fiber protein rather than the chimeric adenovirus protein. Also preferably, the chimeric adenovirus fiber protein may act to increase the specificity of targeting, e.g., by changing the specificity of the fiber protein.

"Efficiency of entry" can be quantitated by several means. In particular, efficiency of entry can be quantitated by introducing a chimeric fiber protein into a vector, preferably a viral vector, and monitoring cell entry (e.g., by vector-mediated delivery to a cell of a gene such as a reporter gene) as a function of multiplicity of infection (MOI). In this case, a reduced MOI required for cell entry of a vector comprising a chimeric adenoviral fiber protein as compared with a vector that is identical, except for comprising a wild-type adenoviral fiber protein rather than said chimeric adenovirus fiber protein, indicates "more efficient" entry.

Similarly, efficiency of entry can be quantitated in terms of the ability of vectors containing chimeric or wild-type fiber proteins, or the soluble chimeric or wild-type fiber proteins themselves, to bind to cells. In this case, increased binding exhibited for the vector containing a chimeric adenoviral fiber protein, or the chimeric fiber protein itself, as compared with the identical vector containing a wild-type fiber protein instead, or the wild-type fiber protein itself, is indicative of an increased efficiency of entry, or "more efficient" entry.

According to this invention, a nonnative amino acid sequence is conformationally-restrained, or "constrained". A nonnative amino acid sequence is constrained when it is present in a chimeric fiber protein and is presented to a cell in such a fashion that the ability of the chimeric fiber protein to bind to the cell and/or mediate cell entry is increased, e.g., relative to the wild-type protein. Such constraint according to the present invention can be achieved by the placement of a nonnative amino acid sequence in an exposed loop of the chimeric fiber protein, or, through the placement of the sequence in another location and creation of a loop-like structure comprising the nonnative amino acid sequence at that site.

Adenoviral-mediated gene delivery to specific tissues (i.e., cell targeting) has been impeded by the fact that, generally, lower affinity, unconstrained peptides often are not as effective in mediating adenovirus binding to target receptors as are constrained peptides. For instance, peptide motifs identified by phage display or identified in generally are presented in a constrained environment. Accordingly, the present application provides a means of targeting adenovirus wherein, in one embodiment, the peptide motifs are presented in the constrained environment of the loop domains of the knob of the adenovirus fiber protein.

This method is advantageous since not all the residues of the exposed fiber knob loops are critical for the assembly or functioning of the fiber protein, and thus provide convenient sites at which the peptide motifs can be inserted. This method further is advantageous in that additions within a loop of a protein structure will be more resistant to proteolytic degradation than will additions in the end of a protein. Moreover, for low affinity peptide motifs in particular, this method is more efficient than the method wherein the peptide motifs are presented as unconstrained linear structures at the C-terminus of the knob of the fiber. Conceivably, "constraint", according to the invention, increases affinity since it puts the molecule in a topological conformation in which it is in sync with its receptor, and, in this fashion, facilitates binding. However, the specification is not limited to any particular mechanism of action and is not to be so construed.

Figure 4:
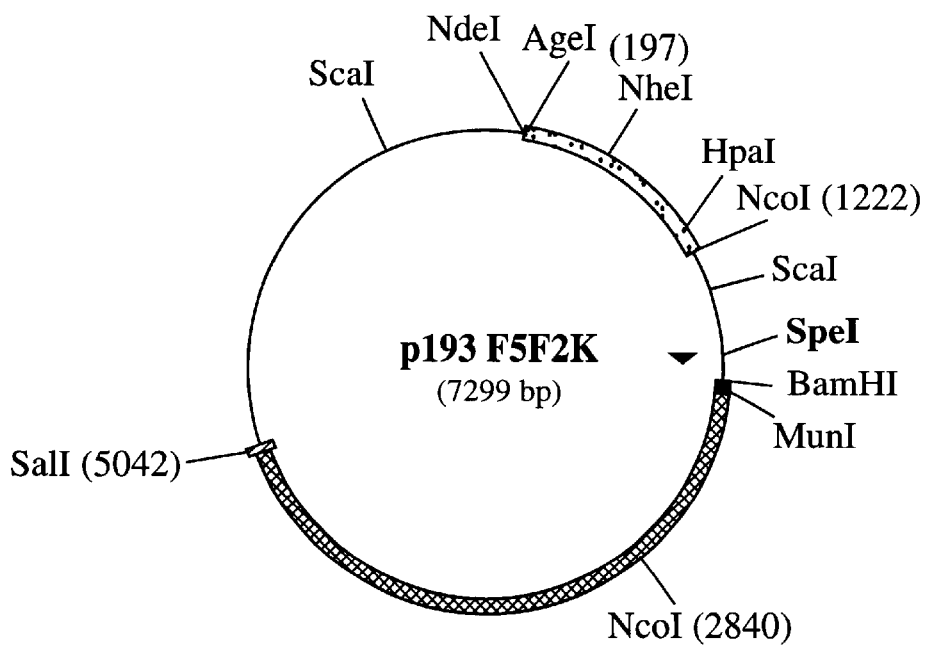
FIG. 4 is a diagram that depicts the plasmid p193 F5F2K, which encodes a chimeric fiber protein.
Figure 5:
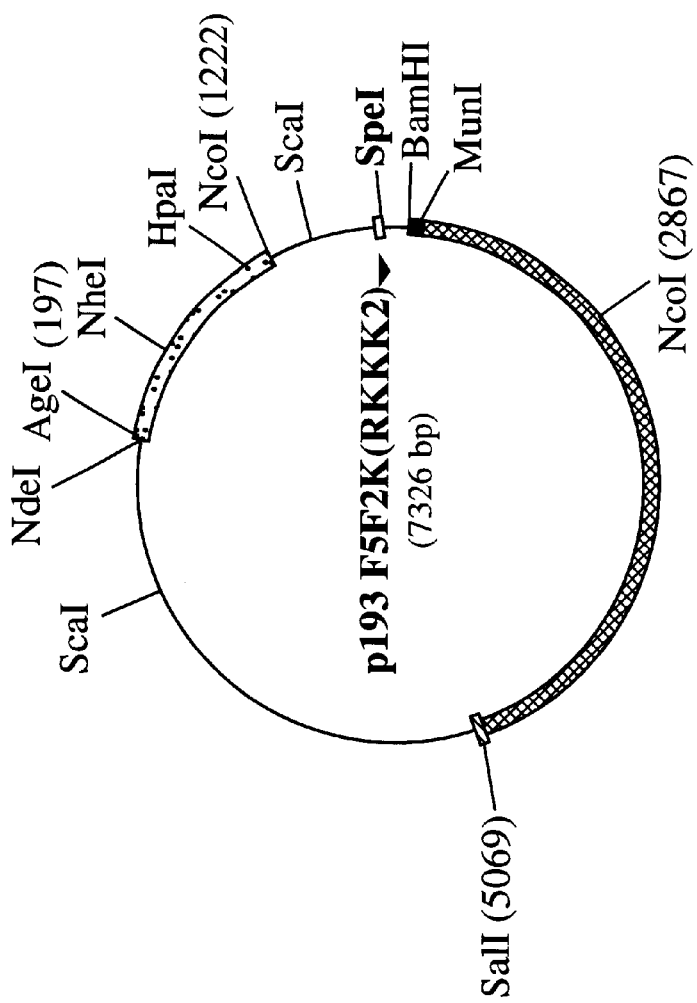
FIG. 5 is a diagram that depicts the plasmid p193 F5F2K (RKKK2), which encodes a chimeric adenovirus fiber protein comprising the heparin binding domain (i.e., RKKKRKKK [SEQ ID NO:1]) in the exposed HI loop of the Ad2 fiber knob.
Figure 6:
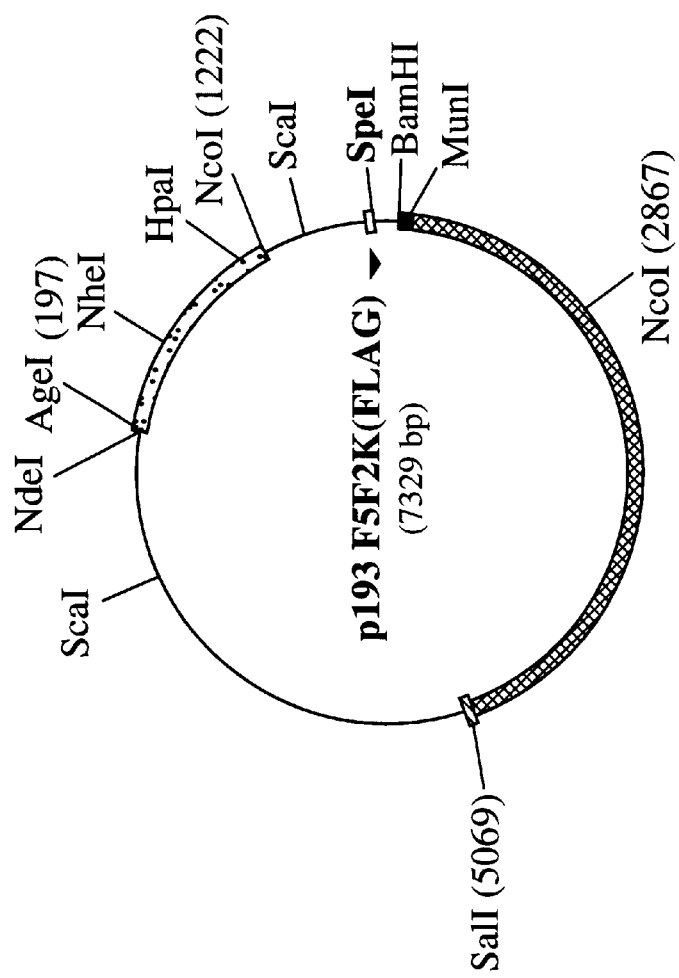
FIG. 6 is a diagram that depicts the plasmid p193 F5F2K (FLAG), which encodes a chimeric adenovirus fiber protein comprising the FLAG epitope (i.e., DYKDDDDK [SEQ ID NO:2]) in the exposed HI loop of the Ad2 fiber knob.

In terms of the loop domains of the fiber knob which can be employed in the context of the invention, the crystal structure of the fiber knob has been described (see, e.g., Xia et al., supra, particularly FIG. 4). The knob monomer comprises an eight-stranded antiparallel β-sandwich fold. The overall structure of the fiber knob trimer resembles a three-bladed propeller with certain β-strands of each of the three monomers comprising the faces of the blades. In particular, the following residues of the Ad5 fiber knob appear important in hydrogen bonding in the β-sandwich motif: 400–402, 419–428, 431–440, 454–461, 479–482, 485–486, 516–521, 529–536, 550–557, and 573–578. The remaining residues of the protein (which do not appear to be critical in forming the fiber protein secondary structure) define the exposed loops of the protein knob domain. In particular, residues inclusive of 403–418 comprise the AB loop, residues inclusive of 441–453 comprise the CD loop, residues inclusive of 487–514 comprise the DG loop, residues inclusive of 522–528 comprise the GH loop, residues inclusive of 537–549 comprise the HI loop and residues inclusive of 558–572 comprise the IJ loop.

According to this invention, "loop" is meant in the generic sense of defining a span of amino acid residues (i.e., more than one, preferably less than two hundred, and even more preferably, less than thirty) that can be substituted by the nonnative amino acid sequence to comprise a peptide motif that allows for cell targeting. While such loops are defined herein with respect to the Ad5 sequence, the sequence alignment of other fiber species have been described (see, e.g., Xia et al., supra). For these other species (particularly Ad2, Ad3, Ad7, Ad40 and Ad41 described in Xia et al., supra), the corresponding loop regions of the knob domains appear to be comparable.

Furthermore, the corresponding residues important in the fiber knob for protein binding/folding appear to be conserved between fiber proteins of different adenoviral serotypes (Xia et al., supra). This suggests that even for those adenoviral species in which the crystal structure of the fiber protein is not known, outside of these conserved residues will lie nonconserved regions, or regions that do not exhibit the high level of conservation observed for the residues critical to protein functionality. Likely the sequence of the fiber knob protein in these nonconserved regions will be present as a loop due to the absence of important intramolecular interactions in this region of the protein. The loop sequences comprising these nonconserved regions similarly can be mutated as described herein by incorporation of peptide motifs allowing cell targeting. These so-called nonconserved sequences likely include any amino acids that occur outside of the conserved regions (i.e., residues non-inclusive of those corresponding to Ad5 residues 400–402, 419–428, 431–440, 454–461, 479–482, 485–486, 516–521, 529–536, 550–557, and 573–578).

More generally, the nonconserved regions will comprise hydrophobic residues that typically are found on the interior of a protein. Such hydrophobic residues include, but are not limited to, Ile, Val, Leu, Trp, Cys, and Phe. In contrast, the conserved regions generally will comprise hydrophilic residues such as charged residues (e.g., Arg, Lys, Glu, Asp, and the like) or polar residues or residues comprising a hydroxyl group (e.g., Thr, Ser, Asn, Gln, etc.). This means that a rough approximation of the exposed and buried amino acids of the fiber protein can be derived based on its hydrophobicity/hydrophilicity plot.

Thus, the present invention preferably provides a chimeric adenovirus fiber protein comprising a constrained nonnative amino acid sequence. Preferably, the nonnative amino acid sequence is constrained by its presence in a loop of the knob of the chimeric fiber protein. In particular, desirably the nonnative amino acid sequence is inserted into or in place of a protein sequence in a loop of the knob of the chimeric adenoviral fiber protein. Optionally, the fiber protein loop is selected from the group consisting of the AB, CD, DG, GH, and IJ loops, and desirably is the HI loop. Also, preferably, the loop comprises amino acid residues in the fiber knob other than Ad5 residues 400–402, 419–428, 431–440, 454–461, 479–482, 485–486, 516–521, 529–536, 550–557, and 573–578. Desirably, the loop comprises amino acid residues selected from the group consisting of residues 403–418, 441–453, 487–514, 522–528, 537–549, and 558–572.

In particular, preferably the nonnative amino acid sequence present in the loop comprises a sequence selected from the group consisting of SEQ ID NO:1, SEQ ID NO:2, SEQ ID NO:3, SEQ ID NO:4, SEQ ID NO:5, SEQ ID NO:17, SEQ ID NO:19, SEQ ID NO:23, SEQ ID NO:31, SEQ ID NO:35, SEQ ID NO:39, SEQ ID NO:43, SEQ ID NO:49, SEQ ID NO:53, SEQ ID NO:56, SEQ ID NO:59, and SEQ ID NO:63, SEQ ID NO:66, SEQ ID NO:67, SEQ ID NO:68, SEQ ID NO:86, and wherein the sequence may be deleted at either the C- or N-terminus by 1, 2, or 3 residues. The nonnative amino acid sequence also desirably can comprise conservative amino acid substitutions of these sequences, as further described herein. Optionally, these sequences can be present in the chimeric protein as depicted, for instance, in FIG. 4, FIG. 5, FIG. 6, FIG. 8, FIG. 9, and FIG. 10.

The invention also provides a means of targeting adenovirus wherein the peptide motifs are presented in a constrained environment at the C-terminus of the fiber protein in the region of the fiber knob. This method entails the generation of loops (i.e., "nonpreexisting loops") by bonding between cysteine residues or through use of other sequences capable of forming loops (e.g., a β-sheet), thereby creating a loop-like secondary structure in the domain of the protein in which the peptide motif is inserted. Generally, according to the invention, the nonnative amino acid sequence being added itself will form a loop-like structure (e.g., through disulfide bonding between cysteine residues occurring in vivo). However, it also is possible that the loop may form due to bonding, e.g., between a cysteine residue present in the nonnative amino acid sequence, and one in the wild-type fiber protein. In this sense, the looping of the sequence is not inherent, but is potential.

In particular, a chimeric adenovirus fiber protein according to the invention comprises a nonnative amino acid sequence that is constrained, preferably by its possession of an RGD peptide (or other similar peptide such as LDV, as described herein) and one or more cysteine pairs. According to this invention, a "pair" comprises two cysteines separated by at least one intervening amino acid. Desirably, when the sequence comprises only a single pair, the cysteines are separated by the RGD sequence (or other similar sequence that can be employed to effect cell targeting, and preferably, is less than 30 amino acids) such that the nonpreexisting loop can be created, i.e., through disulfide bonding. Preferably, the cysteine residues in this case are separated by less than 30 amino acids, for instance, a mixture of glycine and serine residues as in [SEQ ID NO:73]. Regardless of the nonnative amino acid sequence employed, it must comprise a loop -like secondary structure.

In terms of this nonpreexisting loop, one potential peptide motif and variations thereof have been described herein. However, other RGD-containing cyclic peptides have been described in the literature and can be employed in the context of the invention as the nonnative amino acid sequence (see, e.g., Koivunen et al., *Bio/Technology*, 13, 265–270 (1995)). In particular, another nonnative amino acid sequence according to the invention can comprise the sequence CDCRGDCFC ([SEQ ID NO:3]. The nonnative amino acid sequence, however, preferably comprises Cys Xaa Cys Arg Gly Asp Cys Xaa Cys [SEQ ID NO:4] (wherein "Xaa" is any nucleic acid) or Cys(Xaa)$_A$ Cys Arg Gly Asp Cys(Xaa)$_B$ Cys, wherein "A" and "B" can vary independently and can be any number from 0 to 8, so long as either A or B is 1. In particular, the nonnative amino acid sequence preferably comprises the sequence Cys Xaa Xaa Xaa Xaa Xaa Xaa Xaa Xaa Cys Arg Gly Asp Cys Xaa Xaa Xaa Xaa Xaa Xaa Xaa Xaa Cys [SEQ ID NO:5], wherein deletions can be made of amino acid residues other than cysteine on either one or both side(s) of the RGD (i.e., Arg Gly Asp) sequence of 1, 2, 3, 4, 5, 6, 7, or 8 residues.

Thus, desirably the nonnative amino acid sequence comprising the nonpreexisting loop is inserted into or in place of a protein sequence at the C-terminus of the chimeric adenovirus fiber protein. Preferably the nonnative amino acid sequence comprising the nonpreexisting loop is inserted into a loop of the knob of the chimeric adenoviral fiber protein. Optimally the nonnative amino acid sequence comprises a sequence selected from the group consisting of SEQ ID NO:3, SEQ ID NO:4 and SEQ ID NO:5, wherein the sequence may be deleted at either the C- or N-terminus by 1, 2, or 3 residues. The amino acid sequence also desirably can comprise conservative amino acid substitutes of these sequences, as further described herein.

The nonpreexisting loop optionally is attached to the C-terminus of the fiber protein or in a fiber knob loop by means of a so-called "spacer" sequence. The spacer sequence may comprise part of the nonnative amino acid sequence proper, or it may be an entirely separate sequence. In particular, a spacer sequence is a sequence that preferably intervenes between the native protein sequence and the nonnative sequence, between a nonnative sequence and another nonnative sequence, or between a native sequence and another native sequence. Such a sequence desirably is incorporated into the protein to ensure that the nonnative sequence comprising the epitope for an antibody or cell surface binding site projects from the three dimensional structure of the chimeric fiber in such a fashion so as to be able to interact with and bind to cells. A spacer sequence can be of any suitable length, preferably from about 3 to about 30 amino acids, and comprises any amino acids, for instance, a mixture of glycine and serine residues as in [SEQ ID NO:73]. Optimally, the spacer sequence does not interfere with the functioning of the fiber protein.

Nucleic Acid Encoding a Chimeric Adenovirus Fiber Protein

As indicated previously, preferably the nonnative amino acid sequence is introduced at the level of DNA. Accordingly, the invention also provides an isolated and purified nucleic acid encoding a chimeric adenovirus fiber protein comprising a constrained nonnative amino acid sequence according to the invention. Desirably, the nucleic acid sequence that encodes the nonnative amino acid sequence comprises a sequence selected from the group consisting of SEQ ID NO:16, SEQ ID NO:18, SEQ ID NO:22, SEQ ID NO:26, SEQ ID NO:28, SEQ ID NO:30, SEQ ID NO:34, SEQ ID NO:38, SEQ ID NO:42, SEQ ID NO:48, SEQ ID NO:52, SEQ ID NO:56, SEQ ID NO:57, SEQ ID NO:58, and SEQ ID NO:62, as well as conservatively modified variants of these nucleic acid sequences.

A "conservatively modified variant" is a variation on the nucleic acid sequence that results in a conservative amino acid substitution. A "conservative amino acid substitution" is an amino acid substituted by an alternative amino acid of similar charge density, hydrophilicity/hydrophobicity, size, and/or configuration (e.g., Val for Ile). In comparison, a "nonconservatively modified variant" is a variation on the nucleic acid sequence that results in a nonconservative amino acid substitution. A "nonconservative amino acid substitution" is an amino acid substituted by an alternative amino acid of differing charge density, hydrophilicity/ hydrophobicity, size, and/or configuration (e.g., Val for Phe). The means of making such modifications are well known in the art, are described in the Examples which follow, and also can be accomplished by means of commercially available kits and vectors (e.g., New England Biolabs, Inc., Beverly, Mass.; Clontech, Palo Alto, Calif.). Moreover, the means of assessing such substitutions (e.g., in terms of effect on ability to bind and enter cells) are described in the Examples herein. Other approaches described in the art also are available for identifying peptide sequences that can act as ligands for a cell surface receptor and, hence, are of use in the present invention (see, e.g., Russell, *Nature Medicine*, 2, 276–277 (1996)).

The means of making such a chimeric fiber protein, particularly the means of introducing the sequence at the level of DNA, is well known in the art, and is described in the Examples that follow. Briefly, the method comprises introducing a sequence into the sequence encoding the fiber protein so as to insert a new peptide motif into or in place of a protein sequence at the C-terminus of the wild-type fiber protein, or in a loop of a knob of the wild-type fiber protein. Such introduction can result in the insertion of a new peptide binding motif, or creation of a peptide motif (e.g., wherein some of the sequence comprising the motif is already present in the native fiber protein). The method also can be carried out to replace fiber sequences with a nonnative amino acid sequence according to the invention.

Generally, this can be accomplished by cloning the nucleic acid sequence encoding the chimeric fiber protein into a plasmid or some other vector for ease of manipulation of the sequence. Then, a unique restriction site at which further sequences can be added into the fiber protein is identified or inserted into the fiber sequence. A double-stranded synthetic oligonucleotide generally is created from overlapping synthetic single-stranded sense and antisense oligonucleotides such that the double-stranded oligonucleotide incorporates the restriction sites flanking the target sequence and, for instance, can be used to incorporate replacement DNA. The plasmid or other vector is cleaved with the restriction enzyme, and the oligonucleotide sequence having compatible cohesive ends is ligated into the plasmid or other vector to replace the wild-type DNA. Other means of in vitro site-directed mutagenesis such as are known to those skilled in the art, and can be accomplished (in particular, using PCR), for instance, by means of commercially available kits, can also be used to introduce the mutated sequence into the fiber protein coding sequence.

Once the mutated sequence is introduced into the chimeric coat protein, the nucleic acid fragment encoding the sequence can be isolated, e.g., by PCR amplification using 5' and 3' primers, preferably ones that terminate in further unique restriction sites. Use of primers in this fashion results in an amplified chimeric fiber-containing fragment that is flanked by the unique restriction sites. The unique restriction sites can be used for further convenient subcloning of the fragment. Other means of generating a chimeric fiber protein also can be employed. These methods are highly familiar to those skilled in the art.

Vector Comprising a Chimeric Adenovirus Fiber Protein

A "vector" according to the invention is a vehicle for gene transfer as that term is understood by those skilled in the art. Three types of vectors encompassed by the invention are: plasmids, phages, and viruses. Plasmids, phages, and viruses can be transferred to a cell in their nucleic acid form (e.g., via transfection). In comparison, phages and viruses also can be transferred with the nucleic acid in a "capsular" form. Hence, the vectors (e.g., capsular form) that can be employed for gene transfer are referred to herein generally as "vectors", with nucleic acid forms being referred to more particularly as "transfer vectors". However, transfer vectors also are vectors within the context of the invention.

Preferably, a vector according to the invention is a virus, especially a virus selected from the group consisting of nonenveloped viruses, i.e., nonenveloped RNA or DNA viruses. Also, a virus can be selected from the group consisting of enveloped viruses, i.e., enveloped RNA or DNA viruses. Such viruses preferably comprise a fiber protein, or an analogous coat protein that is used for cell entry. Desirably, the viral coat protein is one that projects outward from the capsid such that it is able to interact with cells. In the case of enveloped RNA or DNA viruses, preferably the coat protein is a lipid envelope glycoprotein (i.e., a so-called spike or peplomer).

In particular, preferably a vector is a nonenveloped virus (i.e., either a RNA or DNA virus) from the family Hepadnaviridae, Parvoviridae, Papovaviridae, Adenoviridae, or Picornaviridae. A preferred nonenveloped virus according to the invention is a virus of the family Hepadnaviridae, especially of the genus Hepadnavirus. A virus of the family Parvoviridae desirably is of the genus Parvovirus (e.g., parvoviruses of mammals and birds) or Dependovirus (e.g., adeno-associated viruses (AAVs)). A virus of the family Papovaviridae preferably is of the subfamily Papillomavirinae (e.g., the papillomaviruses including, but not limited to, human papillomaviruses (HPV) 1-48) or the subfamily Polyomavirinae (e.g., the polyomaviruses including, but not limited to, JC, SV40 and BK virus). A virus of the family Adenoviridae desirably is of the genus Mastadenovirus (e.g., mammalian adenoviruses) or Aviadenovirus (e.g., avian adenoviruses). A virus of the family Picornaviridae is preferably a hepatitis A virus (HAV), hepatitis B virus (HBV), or a non-A or non-B hepatitis virus.

Similarly, a vector can be an enveloped virus from the family Herpesviridae or Retroviridae, or can be a Sindbis virus. A preferred enveloped virus according to the invention is a virus of the family Herpesviridae, especially of the subfamily or genus Alphaherpesvirinae (e.g., herpes simplex-like viruses), Simplexvirus (e.g., herpes simplex-like viruses), Varicellavirus (e.g., varicella and pseudorabies-like viruses), Betaherpesvirinae (e.g., the cytomegaloviruses), Cytomegalovirus (e.g., the human cytomegaloviruses), Gammaherpesvirinae (e.g., the lymphocyte-associated viruses), and Lymphocryptovirus (e.g., EB-like viruses).

Another preferred enveloped virus is a RNA virus of the family Retroviridae (i.e., a retrovirus), particularly a virus of the genus or subfamily Oncovirinae, Spumavirinae, Spumavirus, Lentivirinae, or Lentivirus. A RNA virus of the subfamily Oncovirinae is desirably a human T-lymphotropic virus type 1 or 2 (i.e., HTLV-1 or HTLV-2) or bovine leukemia virus (BLV), an avian leukosis-sarcoma virus (e.g., Rous sarcoma virus (RSV), avian myeloblastosis virus (AMV), avian erythroblastosis virus (AEV), Rous-associated virus (RAV)-1 to 50, RAV-0), a mammalian C-type virus (e.g., Moloney murine leukemia virus (MuLV), Harvey murine sarcoma virus (HaMSV), Abelson murine leukemia virus (A-MuLV), AKR-MuLV, feline leukemia virus (FeLV), simian sarcoma virus, reticuloendotheliosis virus (REV), spleen necrosis virus (SNV)), a B-type virus (e.g., mouse mammary tumor virus (MMTV)), or a D-type virus (e.g., Mason-Pfizer monkey virus (MPMV), "SAIDS" viruses). A RNA virus of the subfamily Lentivirus is desirably a human immunodeficiency virus type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. The acronym "HIV" or terms "AIDS virus" or "human immunodeficiency virus" are used herein to refer to these HIV viruses, and HIV-related and -associated viruses, generically. Moreover, a RNA virus of the subfamily Lentivirus preferably is a Visna/maedi virus (e.g., such as infect sheep), a feline immunodeficiency virus (FIV), bovine lentivirus, simian immunodeficiency virus (SIV), an equine infectious anemia virus (EIAV), or a caprine arthritis-encephalitis virus (CAEV).

An especially preferred vector according to the invention is an adenoviral vector (i.e., a viral vector of the family Adenoviridae, optimally of the genus Mastadenovirus). Desirably such a vector is an Ad2 or Ad5 vector, although other serotype adenoviral vectors can be employed. Adenoviral stocks that can be employed according to the invention include any of the adenovirus serotypes 1 through 47 currently available from American Type Culture Collection (ATCC, Rockville, Md.), or from any other serotype of adenovirus available from any other source. For instance, an adenovirus can be of subgroup A (e.g., serotypes 12, 18, 31), subgroup B (e.g., serotypes 3, 7, 11, 14, 16, 21, 34, 35), subgroup C (e.g., serotypes 1, 2, 5, 6), subgroup D (e.g., serotypes 8, 9, 10, 13, 15, 17, 19, 20, 22–30, 32, 33, 36–39, 42–47), subgroup E (serotype 4), subgroup F (serotype 40, 41), or any other adenoviral serotype.

The adenoviral vector employed for gene transfer can be wild-type (i.e., replication competent). Alternately, the adenoviral vector can comprise genetic material with at least one modification therein, which can render the virus replication deficient. The modification to the adenoviral genome can include, but is not limited to, addition of a DNA segment, rearrangement of a DNA segment, deletion of a DNA segment, replacement of a DNA segment, or introduction of a DNA lesion. A DNA segment can be as small as one nucleotide and as large as 36 kilobase pairs (i.e., the approximate size of the adenoviral genome) or, alternately, can equal the maximum amount which can be packaged into an adenoviral virion (i.e., about 38 kb). Preferred modifications to the adenoviral genome include modifications in the E1, E2, E3 and/or E4 region. An adenoviral vector also preferably can be a cointegrated, i.e., a ligation of adenoviral genomic sequences with other sequences, such as other virus, phage, or plasmid sequences.

In terms of a viral vector (e.g., particularly a replication deficient adenoviral vector), such a vector can comprise either complete capsids (i.e., including a viral genome such as an adenoviral genome) or empty capsids (i.e., in which a viral genome is lacking, or is degraded, e.g., by physical or chemical means). Preferably the viral vector comprises complete capsids. Along the same lines, since methods are available for transferring viruses, plasmids, and phages in the form of their nucleic acid sequences (i.e., RNA or DNA), a vector (i.e., a transfer vector) similarly can comprise RNA or DNA, in the absence of any associated protein such as capsid protein, and in the absence of any envelope lipid. Thus, according to the invention whereas a vector "comprises" a chimeric adenoviral fiber protein, a transfer vector comprises a chimeric adenoviral fiber protein in the sense that it "encodes" the chimeric adenoviral fiber protein.

A vector according to the invention can comprise additional sequences and mutations, e.g., some within the fiber protein itself. For instance, a vector according to the invention firther preferably comprises a nucleic acid comprising a passenger gene.

A "nucleic acid" is a polynucleotide (DNA or RNA). A "gene" is any nucleic acid sequence coding for a protein or a nascent RNA molecule. A "passenger gene" is any gene which is not typically present in and is subcloned into a vector (e.g., a transfer vector) according to the present invention, and which upon introduction into a host cell is accompanied by a discernible change in the intracellular environment (e.g., by an increased level of deoxyribonucleic acid (DNA), ribonucleic acid (RNA), peptide or protein, or by an altered rate of production or degradation thereof). A "gene product" is either an as yet untranslated RNA molecule transcribed from a given gene or coding sequence (e.g., MRNA or antisense RNA) or the polypeptide chain (i.e., protein or peptide) translated from the MRNA molecule transcribed from the given gene or coding sequence. Whereas a gene comprises coding sequences plus any non-coding sequences, a "coding sequence" does not include any non-coding (e.g., regulatory) DNA. A gene or coding sequence is "recombinant" if the sequence of bases along the molecule has been altered from the sequence in which the gene or coding sequence is typically found in nature, or if the sequence of bases is not typically found in nature. According to this invention, a gene or coding sequence can be wholly or partially synthetically made, can comprise genomic or complementary DNA (cDNA) sequences, and can be provided in the form of either DNA or RNA.

Non-coding sequences or regulatory sequences include promoter sequences. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which are also termed "promoter elements") in that enhancers can function in either orientation, and over distances of up to several kilobase pairs, even from a position downstream of a transcribed region. According to the invention, a coding sequence is "operably linked" to a promoter (e.g., when both the coding sequence and the promoter constitute a passenger gene) when the promoter is capable of directing transcription of that coding sequence.

Accordingly, a "passenger gene" can be any gene, and desirably is either a therapeutic gene or a reporter gene. Preferably a passenger gene is capable of being expressed in a cell in which the vector has been internalized. For instance, the passenger gene can comprise a reporter gene, or a nucleic acid sequence which encodes a protein that can in some fashion be detected in a cell. The passenger gene also can comprise a therapeutic gene, for instance, a therapeutic gene which exerts its effect at the level of RNA or protein. For instance, a protein encoded by a transferred therapeutic gene can be employed in the treatment of an inherited disease, such as, e.g., the cystic fibrosis transmembrane conductance regulator cDNA for the treatment of cystic fibrosis. The protein encoded by the therapeutic gene may exert its therapeutic effect by resulting in cell killing. For instance, expression of the gene in itself may lead to cell killing, as with expression of the diphtheria toxin A gene, or the expression of the gene may render cells selectively sensitive to the killing action of certain drugs, e.g., expression of the HSV thymidine kinase gene renders cells sensitive to antiviral compounds including acyclovir, gancyclovir and FIAU (1-(2-deoxy-2-fluoro-β-D-arabinofuranosil)-5-iodouracil).

Moreover, the therapeutic gene can exert its effect at the level of RNA, for instance, by encoding an antisense message or ribozyme, a protein which affects splicing or 3' processing (e.g., polyadenylation), or can encode a protein which acts by affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Accordingly, the use of the term "therapeutic gene" is intended to encompass these and any other embodiments of that which is more commonly referred to as gene therapy as known to those of skill in the art. Similarly, the recombinant adenovirus can be used for gene therapy or to study the effects of expression of the gene in a given cell or tissue in vitro or in vivo.

The present invention accordingly provides a vector comprising a chimeric adenovirus fiber protein that comprises a constrained nonnative amino acid sequence. Such a vector preferably comprises a passenger gene which optionally is either inserted into the adenoviral genome or is attached to a coat protein (i.e., penton base, fiber, or hexon protein) of the adenovirus by means of a protein/DNA interaction. Alternately, the adenoviral vector preferably carries into a cell an unlinked DNA or protein molecule, or other small moiety, by means of adenovirus bystander-mediated uptake of these molecules (International Patent Application WO 95/21259).

Along these lines, the method of the invention can be employed to transfer nucleic acid sequences which are transported as part of the adenoviral genome (i.e., encoded by adenovirus), and to transfer nucleic acid sequences that are attached to the outside of the adenoviral capsid (Curiel et al., supra), as well as unattached DNA, protein, or other small molecules that similarly can be transported by adenoviral bystander-mediated uptake (International Patent Application WO 95/21259). The method can be employed to mediate gene and/or protein delivery either ex vivo or in vivo, as described herein.

Desirably, a vector is a viral vector selected from the group consisting of nonenveloped viruses. Such a vector desirably comprises a nonnative amino acid sequence according to the invention and/or a nucleic acid sequence that encodes such nonnative amino acid sequence. Optimally, the vector is an adenoviral vector, particularly an adenoviral vector selected from the group consisting of AdZ.FLAG, AdZ.RKKK2, AdZ.pGS, AdZ.RGD, AdZ.pRGD, AdZ.pLDV, and AdZ.pYIGSR.

The means of making the recombinant adenoviral vectors according to the invention are known to those skilled in the art. For instance, recombinant adenovirus comprising a chimeric fiber protein and the recombinant adenovirus that additionally comprises a passenger gene or genes capable of being expressed in a particular cell can be generated by use of a transfer vector, preferably a viral or plasmid transfer vector, in accordance with the present invention. Such a transfer vector preferably comprises a chimeric adenoviral fiber sequence as previously described. The chimeric fiber protein gene sequence comprises a nonnative (i.e., non-wild-type) sequence in place of the native sequence, which has been deleted, or in addition to the native sequence.

A recombinant chimeric fiber protein gene sequence can be moved to or from an adenoviral vector from or into a baculovirus or a suitable prokaryotic or eukaryotic expression vector for expression and evaluation of receptor or protein specificity and avidity, trimerization potential, penton base binding, and other biochemical characteristics. In particular, the method of protein production in baculovirus as set forth in the Examples which follow, and as described in Wickham et al. (1995), supra, can be employed.

Accordingly, the present invention also provides recombinant baculoviral and prokaryotic and eukaryotic expression vectors comprising a chimeric adenoviral fiber protein gene sequence, which also can be transfer vectors. The present invention also provides vectors that fall under a commonly employed definition of transfer vectors, e.g., vectors which are plasmids containing adenovirus sequences that are used to create new adenovirus vectors. The chimeric fiber protein gene sequence includes a nonnative sequence in addition to or in place of a native amino acid sequence. This enables the resultant chimeric fiber protein to bind to a binding site other than a binding site bound by the native sequence. By moving the chimeric gene from an adenoviral transfer vector to baculovirus or a prokaryotic or eukaryotic expression vector, high protein expression is achievable (approximately 5–50% of the total protein being the chimeric fiber). Preferred transfer vectors according to the invention are selected from the group consisting of p193 (F5*), p193 F5F2K(FLAG), p193 F5F2K, p193 F5F2K (RKKK2), p193(F5)pGS(RGD), p193(F5)pLDV, p193(F5) pYIGSR, and p193(F5*)RGD.

A vector according to the invention further can comprise, either within, in place of, or outside of the coding sequence of a fiber protein additional sequences that impact upon the ability of the fiber protein to trimerize, or comprise a protease recognition sequence. A sequence that impacts upon the ability to trimerize is one or more sequences that enable fiber trimerization. A sequence that comprises a protease recognition sequence is a sequence that can be cleaved by a protease, thereby effecting removal of the chimeric coat protein (or a portion thereof) and attachment of the recombinant adenovirus to a cell by means of another coat protein. When employed with a fiber protein, the protease recognition site preferably does not affect fiber trimerization or receptor specificity of the fiber protein. For instance, in one embodiment of the present invention, preferably the fiber protein, or a portion thereof, is deleted by means of a protease recognition sequence, and then the penton base protein, or another protein, commands cell binding/cell entry.

In terms of the production of vectors and transfer vectors according to the invention, transfer vectors are constructed using standard molecular and genetic techniques such as are known to those skilled in the art. Vectors comprising virions or virus particles are produced using viral vectors in the appropriate cell lines. Similarly, the adenoviral fiber chimera-containing particles are produced in standard cell lines, e.g., those currently used for adenoviral vectors. Following production and purification, the particles in which fiber is to be deleted are rendered fiberless through digestion of the particles with an appropriate sequence-specific protease, which cleaves the fiber proteins and releases them from the viral particles to generate fiberless particles.

Illustrative Uses

The present invention provides a chimeric fiber protein that is able to bind to cells and mediate entry into cells with high efficiency, as well as vectors and transfer vectors comprising same. The chimeric fiber protein itself has multiple uses, e.g., as a tool for studies in vitro of adenovirus binding to cells (e.g., by Scatchard analysis as shown previously by Wickham et al. (1993), supra), to block binding of adenovirus to receptors in vitro (e.g., by using antibodies, peptides, and enzymes, as described in the Examples herein and as known in the art), and, with use of some chimeric fiber proteins comprising particular peptide motifs, to protect against adenoviral infection in vivo by competing for binding to the binding site by which adenovirus effects cell entry.

A vector comprising a chimeric fiber protein also can be used in strain generation and as a means of making new vectors. For instance, the nonnative amino acid sequence can be introduced intracellularly as a means of generating new vectors via recombination. Similarly, a vector can be used in gene therapy. For instance, a vector of the present invention can be used to treat any one of a number of diseases by delivering to targeted cells corrective DNA, i.e., DNA encoding a function that is either absent or impaired, or a discrete killing agent, e.g., DNA encoding a cytotoxin that, for example, is active only intracellularly. Diseases that are candidates for such treatment include, for example, cancer, e.g., melanoma, glioma or lung cancers; genetic disorders, e.g., cystic fibrosis, hemophilia or muscular dystrophy; pathogenic infections, e.g., human immunodeficiency virus, tuberculosis or hepatitis; heart disease, e.g., preventing restenosis following angioplasty or promoting angiogenesis to reperfuse necrotic tissue; and autoimmune disorders, e.g., Crohn's disease, colitis or rheumatoid arthritis.

In particular, gene therapy can be carried out in the treatment of diseases, disorders, or conditions associated with different tissues that, prior to the present invention, adenovirus was not able to bind to and enter, or could do so only with low affinity and/or specificity. For instance, the method can be employed to incorporate a targeting sequence which permits an increased efficiency of gene delivery to different tissues. Such targeting sequences include, but are not limited to: a heparin binding domain (e.g., polyK, polyR, or combinations thereof); an integrin binding domain (e.g., RGD, LDV, and the like); a laminin receptor domain (e.g., YIGSR [SEQ ID NO:66]); a DNA binding domain (e.g., polyK, polyR, or combinations thereof); antibody epitopes (e.g., the FLAG peptide DYKDDDDK [SEQ ID NO:2] or other epitope); a brain-specific targeting domain (e.g., SLR); and any other peptide domain which binds to a receptor (e.g., in particular, a peptide domain ranging from about 2 to 200 amino acids).

Along these lines, the method can be employed to increase the efficiency of adenoviral-mediated delivery to, for instance, bone marrow cells, endothelium, organs such as lung, liver, spleen, kidneys, brain, eye, heart, muscle, and the like, hematopoietic cells, tumor vasculature, and tumor cells. Diseases, disorders, or conditions associated with these tissues include, but are not limited to angiogenesis, restenosis, inflammation, cancers, Alzheimer's disease, human immunodeficiency virus (HIV-1, HIV-2) infection, and anemias.

These aforementioned illustrative uses are by no means comprehensive, and it is intended that the present invention encompasses such further uses which flow from, but are not explicitly recited in the disclosure herein. Similarly, there are numerous advantages associated with the use of the various aspects of the present invention.

For instance, with incorporation of antibody epitopes into the fiber protein, if the antibody epitope is in a loop close to the fiber receptor binding domain, then binding of the bispecific antibody will block normal receptor binding, thereby increasing the specificity of cell targeting using the antibody epitope. If the fiber receptor binding domain is mutated such that it no longer binds its receptor, then incorporation of specific receptor binding domains into the loop will allow targeting to those tissues that express the complementary receptor in the absence of any competing binding mediated by the wild-type fiber receptor binding domain.

Similarly, a domain which permits inactivation of fiber for its normal receptor binding also can be incorporated into an exposed loop of the fiber protein. Inactivation of the fiber binding to its normal receptor will permit specific targeting via another protein or domain of adenovirus. For instance, $\alpha_v$ integrin targeting with native penton base can be accomplished in this fashion. Along these lines, an enterokinase cleavage site (e.g., DYKDDDDK [SEQ ID NO:2]) or trypsin cleavage site (e.g., RKKKRKKK [SEQ ID NO:1]) can be incorporated into a fiber loop followed by treatment of adenoviral particles with enterokinase or trypsin. Native adenovirus particles are immune to such enterokinase or trypsin treatment.

Furthermore, a vector according to the invention, particularly an adenoviral vector, is advantageous in that it can be isolated and purified by conventional means. Since changes in the vector are made at the genome level, there are no cumbersome and costly post-production modifications required, as are associated with other vectors (see, e.g., Cotten et al., *Proc. Natl. Acad. Sci.*, 89, 6094–6098 (1992); Wagner et al., *Proc. Natl. Acad. Sci.*, 89, 6099–6103 (1992)). Similarly, special adenoviral receptor-expressing cell lines are not required. An adenoviral vector comprising the chimeric fiber protein can be propagated to similar titers as a wild-type vector lacking the fiber modification.

Means of Administration

The vectors and transfer vectors of the present invention can be employed to contact cells either in vitro or in vivo. According to the invention "contacting" comprises any means by which a vector is introduced intracellularly; the method is not dependent on any particular means of introduction and is not to be so construed. Means of introduction are well known to those skilled in the art, and also are exemplified herein.

Accordingly, introduction can be effected, for instance, either in vitro (e.g., in an ex vivo type method of gene therapy or in tissue culture studies) or in vivo by electroporation, transformation, transduction, conjugation or triparental mating, (co-)transfection, (co-)infection, membrane fusion with cationic lipids, high velocity bombardment with DNA-coated microprojectiles, incubation with calcium phosphate-DNA precipitate, direct microinjection into single cells, and the like. Similarly, the vectors can be introduced by means of cationic lipids, e.g., liposomes. Such liposomes are commercially available (e.g., Lipofectin, Lipofectamine™, and the like, supplied by Life Technologies, Gibco BRL, Gaithersburg, Md.). Moreover, liposomes having increased transfer capacity and/or reduced toxicity in vivo (see, e.g., International Patent Application WO 95/21259) can be employed in the present invention. Other methods also are available and are known to those skilled in the art.

According to the invention, a "host" (and thus a "cell" from a host) encompasses any host into which a vector of the invention can be introduced, and thus encompasses an animal, including, but not limited to, an amphibian, bird, fish, insect, reptile, or mammal. Optimally a host is a mammal, for instance, rodent, primate (such as chimpanzee, monkey, ape, gorilla, orangutan, or gibbon), feline, canine, ungulate (such as ruminant or swine), as well as, in particular, human. Desirably such a host cell is one in which an adenovirus can exist for a period of time (i.e., typically from anywhere up to, and potentially even after, about two months) after entry into the cell.

A cell can be present as a single entity, or can be part of a larger collection of cells. Such a "larger collection of cells" can comprise, for instance, a cell culture (either mixed or pure), a tissue (e.g., epithelial or other tissue), an organ (e.g., heart, lung, liver, gallbladder, urinary bladder, eye, and other organs), an organ system (e.g., circulatory system, respiratory system, gastrointestinal system, urinary system, nervous system, integumentary system or other organ system), or an organism (e.g., a bird, mammal, or the like).

Preferably, the peptide binding motif employed for cell targeting is such that the organs/tissues/cells being targeted are of the circulatory system (e.g., including, but not limited to heart, blood vessels, and blood), respiratory system (e.g., nose, pharynx, larynx, trachea, bronchi, bronchioles, lungs, and the like), gastrointestinal system (e.g., including mouth, pharynx, esophagus, stomach, intestines, salivary glands, pancreas, liver, gallbladder, and others), urinary system (e.g., such as kidneys, ureters, urinary bladder, urethra, and the like), nervous system (e.g., including, but not limited to brain and spinal cord, and special sense organs such as the eye) and integumentary system (e.g., skin). Even more preferably, the cells being targeted are selected from the group consisting of heart, hematopoietic, lung, liver, spleen, kidney, brain, eye, bone marrow, endothelial, muscle, tumor vasculature, and tumor cells.

One skilled in the art will appreciate that suitable methods of administering a vector (particularly an adenoviral vector) of the present invention to an animal for purposes of gene therapy (see, for example, Rosenfeld et al., *Science,* 252, 431–434 (1991); Jaffe et al., *Clin. Res.,* 39(2), 302A (1991); Rosenfeld et al., *Clin. Res.,* 39(2), 311A (1991); Berkner, *BioTechniques,* 6, 616–629 (1988); Crystal et al., *Human Gene Ther.,* 6, 643–666 (1995); Crystal et al., *Human Gene Ther.,* 6, 667–703 (1995)), chemotherapy, and vaccination are available, and, although more than one route can be used for administration, a particular route can provide a more immediate and more effective reaction than another route. Pharmaceutically acceptable excipients also are well-known to those who are skilled in the art, and are readily available. The choice of excipient will be determined in part by the particular method used to administer the recombinant vector. Accordingly, there is a wide variety of suitable formulations for use in the context of the present invention. The following methods and excipients are merely exemplary and are in no way limiting.

Moreover, to optimize the ability of the adenovirus to enter the cell by the method of the invention, preferably the method is carried out in the absence of neutralizing antibodies directed against the particular adenovirus being introduced intracellularly. In the absence of such antibodies, there is no possibility of the adenovirus being bound by the antibody, and thus impeded from binding and/or entering the cell. It is well within the ordinary skill of one in the art to test for the presence of such neutralizing antibodies. Techniques that are known in the art can be employed to prevent the presence of neutralizing antibodies from impeding effective protein production (see, e.g., Crompton et al., supra, International Patent Application WO 96/12406).

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

A vector or transfer vector of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, a vector or transfer vector of the present invention can be made into suppositories by mixing with a variety of bases such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, and the particular site and organism being treated. However, the dose should be sufficient to effect a therapeutic response.

As previously indicated, a vector or a transfer vector of the present invention also has utility in vitro. Such a vector can be used as a research tool in the study of adenoviral attachment and infection of cells and in a method of assaying binding site-ligand interaction. Similarly, the chimeric fiber protein comprising a constrained nonnative amino acid sequence in addition to or in place of a native amino acid sequence can be used in receptor-ligand assays and as adhesion proteins in vitro or in vivo, for example.

EXAMPLES

The following examples further illustrate the present invention and, of course, should not be construed as in any way limiting its scope.

Example 1

This example describes the construction of transfer vectors encoding fiber sequences having insertions of various peptide motifs in an exposed loop of the knob region of the adenovirus fiber protein.

The fiber proteins of Ad2 and Ad5 both recognize the same receptor. A parallel evaluation of the protein structure of the fiber knob and its DNA restriction map reveals that the Ad2 fiber knob contains a unique Spe I restriction site in a region encoding an exposed loop in the protein. The amino acids in this loop are not involved in any interactions relevant to protein folding. Accordingly, additions to this loop are highly unlikely to affect the ability of the fiber protein to fold. Chimeric adenoviral fiber proteins comprising modifications of an exposed loop (particularly the HI loop) were constructed as described herein.

For vector construction and characterization, standard molecular and genetic techniques, such as the generation of strains, plasmids, and viruses, gel electrophoresis, DNA manipulations including plasmid isolation, DNA cloning and sequencing, Western blot assays, and the like, were performed such as are known to those skilled in the art, and as are described in detail in standard laboratory manuals (e.g., Maniatis et al., *Molecular Cloning: A Laboratory Manual*, 2nd ed. (Cold Spring Harbor, N.Y., 1992); Ausubel et al., *Current Protocols in Molecular Biology* (1987)). Restriction enzymes and other enzymes used for molecular manipulations were purchased from commercial sources (e.g., Boehringer Mannheim, Inc., Indianapolis, Ind.; New England Biolabs, Beverly, Mass.; Bethesda Research Laboratories, Bethesda, Md.), and were used according to the recommendations of the manufacturer. Cells employed for experiments (e.g., cells of the transformed human embryonic kidney cell line 293 (i.e., CRL 1573 cells) and other cells supplied by American Type Culture Collection) were cultured and maintained using standard sterile culture reagents, media and techniques, as previously described (Erzerum et al., *Nucleic Acids Research*, 21, 1607–1612 (1993)).

Figure 2:
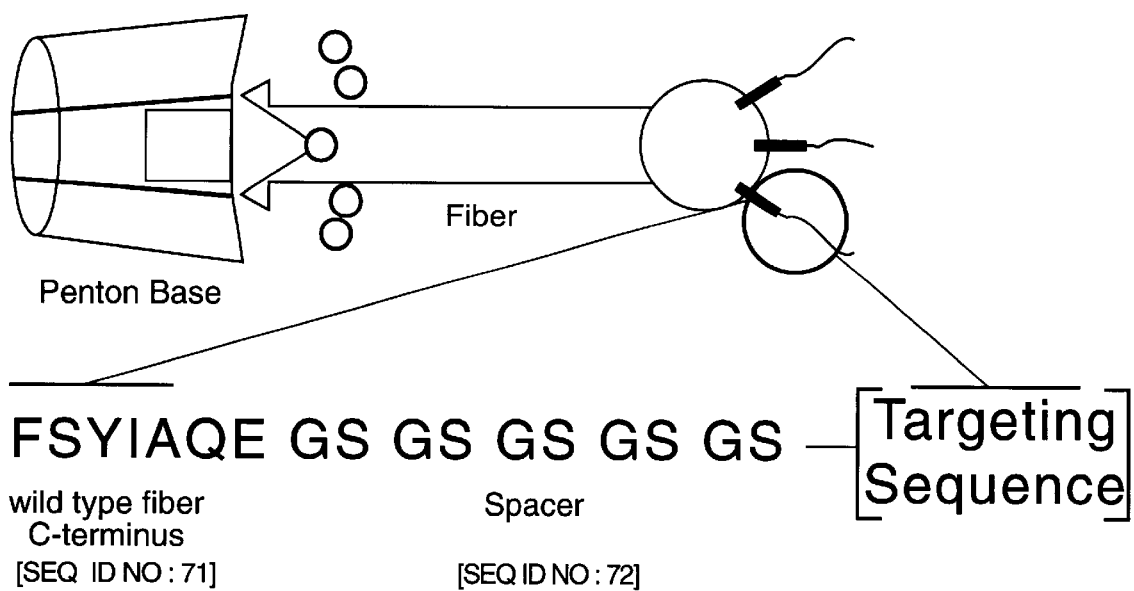
FIG. 2 is a diagram that illustrates the method of the invention of targeting adenovirus by incorporating a conformationally restrained nonnative amino acid sequence (i.e., a sequence comprising a nonpreexisting loop) into the C-terminus of the fiber protein to comprise a peptide binding motif.

In order to make recombinant adenovirus vectors containing targeting sequences, it was first necessary to exchange the knob region of the Ad5 present in a transfer vector with the knob coding region from Ad2, since the HI loop of Ad2 comprises a unique Spe I restriction site, which allows cloning of particular targeting sequences into this site. Accordingly, the net result of the vector manipulations was to create a fiber chimera in which the DNA encoding the tail and shaft of the fiber are from Ad5, the DNA encoding the knob is from Ad2, and the knob further comprises a nonnative amino acid sequence in the HI loop as depicted in FIG. 1. In an alternate method of the invention described in later Examples, the targeting sequence is placed at the terminus of the fiber knob protein, as depicted in FIG. 2.

Figure 3:
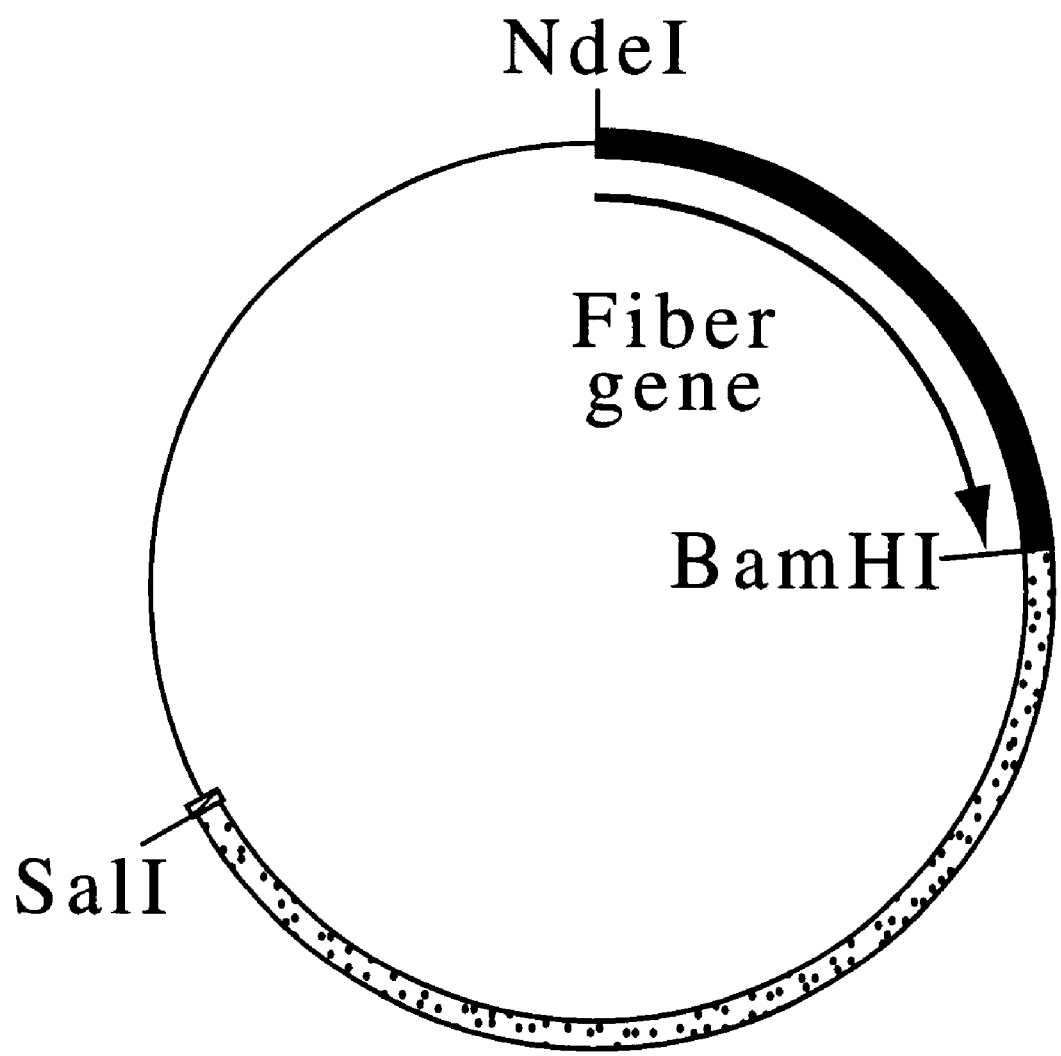
FIG. 3 is a diagram that depicts the plasmid p193(F5*) used to construct adenovirus fiber chimeras.

In the first step of the process of making fiber knob insertions in a loop, the transfer vector p193(F5*) depicted in FIG. 3 was constructed. This plasmid contains an 8 nucleotide insertion between the last amino acid codon of the fiber coding sequence and the stop codon. The 8 nucleotide insertion contains a unique Bam HI restriction site which allows a straightforward replacement of Ad5 fiber domains with other fiber domains from other adenovirus serotypes. Namely, the sequence of the wild-type Ad5 fiber gene is indicated in SEQ ID NOs:6 and 7. In comparison, the C-terminus of the mutated fiber gene present in p193(F5*) is set forth in SEQ ID NOs: 8 and 9:

The transfer plasmid p 193(F5*) was constructed from pl 93NS(ΔF). The mutated fiber gene (i.e., the fiber gene comprising the Bam HI site prior to the stop codon) was incorporated into the fiber-minus plasmid p193NS(ΔF) using synthetic sense and antisense oligonucleotide primers to amplify the fiber gene by means of the polymerase chain reaction (PCR) while at the same time incorporating a modified Bam HI site following the last codon of the fiber gene to create the mutant fiber gene. The primers used to amplify from the Nde I site to the C-terminal coding regions of the fiber gene from Ad5 genome DNA were: antisense primer, T CCC CCC GGG TCT AGA TTA <u>GGA TCC</u> TTC TTG GGC AAT GTA TGA (Bam HI site underlined) [SEQ ID NO:10]; sense primer CGT GTA TC<u>C ATA TGA</u> CAC AGA (Nde I site underlined) [SEQ ID NO:11]. The PCR product was then cut with Nde I and Bam HI and cloned into the Nde I/Bam HI sites of p193NS(ΔF).

The plasmid p193NS(ΔF) itself was constructed by means of an intermediary series of vectors. Namely, first, the transfer plasmid p193NS83-100 was constructed by cloning the Ad5 Nde I to Sal I fragment, which spans the 83–100 map unit region of the Ad5 genome containing the fiber gene, into the plasmid pNEB 193 (New England Biolabs, Beverly, Mass.). The Nde I-Mun I fragment was replaced with a synthetic oligonucleotide comprising a Bam HI site, which was flanked by a 5' Nde I site and a 3' Mun I site to facilitate cloning. The double-stranded synthetic oligonucleotide fragment was created from the overlapping synthetic single-stranded sense (comprising SEQ ID NO:12) and antisense (comprising SEQ ID NO:13) oligonucleotide. The ends of the overlapping oligomers were made to have overhangs compatible for direct cloning into the Nde I and Mun I sites. The resultant vector p193NS(ΔF) lacks all the coding sequence for the fiber gene but contains the entire adenovirus E4 coding sequence. The plasmid retains the AATAAA polyadenylation signal included in the synthetic Nde I/Mun I oligonucleotide and also incorporates the new Bam HI restriction site (underlined).

Thus, following its construction in a series of sequential cloning steps, the transfer vector p193(F5*) was employed in subsequent vector constructions. Namely, the sense oligonucleotide F5F2K(s)N (comprising SEQ ID NO:14 and containing a Nco I restriction site) and the antisense oligonucleotide primer F5F2K(a)B (i.e., comprising SEQ ID NO:15 and containing a Bam HI restriction site) were used to amplify the knob coding region from purified Ad2 DNA by means of PCR. The incorporation of these sites on either end of the PCR product permitted it to be cut with Nco I and Bam HI and cloned into the base plasmid p193(F5*) to create the transfer vector p193 F5F2K depicted in FIG. 4. Unlike p193(F5*), p193 F5F2K contains a unique Spe I restriction site within the Ad2 fiber gene encoding an exposed loop in the protein. Namely, the fiber gene present in p193 F5F2K comprises the mutated fiber sequence (SEQ ID NOs: 16 and 17) including a novel Spe I site introduced into the fiber gene.

This vector was then used to clone targeting sequences into the Spe I site. In particular, a nucleic sequence encoding the FLAG peptide motif [SEQ ID NO:2] and a nucleic acid sequence encoding the stretch of 8 basic amino acids [SEQ ID NO:1] comprising the heparin binding domain were cloned into the Spe I site of pl93 F5F2K using overlapping sense and antisense oligonucleotides.

The PolyGS(RKKK)$_2$ sequence comprises SEQ ID NOs: 18 and 19. The 27-mer sense oligonucleotide PolyGS (RKKK)$_2$(s)(comprising SEQ ID NO:20) and 27-mer antisense oligonucleotide PolyGS(RKKK)$_2$(a) (comprising SEQ ID NO:21) were employed for cloning the PolyGS (RKKK)$_2$ sequence. This plasmid was constructed by cloning the DNA sequence encoding the binding domain into the Spe I site of p193 F5FK2. The overlapping sense and antisense oligonucleotides encoding the binding domain were first annealed and then directly ligated into the Spe I restriction site to result in the plasmid pl93 F5F2K(RKKK2) depicted in FIG. 5.

Similarly, the FLAG sequence comprises SEQ ID NO2:22 and 23. The 30-mer sense oligonucleotide FLAG(s) (comprising SEQ ID NO:24) and 30-mer antisense oligonucleotide FLAG(a) (comprising SEQ ID NO:25) were employed for cloning the FLAG peptide sequence in a similar fashion as for p193 F5F2K(RKKK2) to result in the plasmid p193 F5F2K(FLAG) depicted in FIG. 6.

The FLAG sequence is recognized by the anti-FLAG M2 antibody (Kodak, New Haven, Conn.) and is used for targeting adenovirus by means of bispecific antibodies (Wickham et al., "Targeted Adenovirus Gene Transfer to Endothelial and Smooth Muscle Cells Using Bispecific Antibodies", *J. Virol.*, 70(10), in press (1996)). The RKKKRKKK peptide sequence (SEQ ID NO:21) recognizes cellular heparin sulfate and is used to target the adenovirus to heparin sulfate-containing receptors on cells. Because heparin sulfate moieties are expressed on nearly all mammalian cells, the heparin-binding motif permits AdF2K (RKKK2) to bind to and transduce a broad spectrum of cells, as compared to unmodified (i.e., wild-type) adenovirus vectors.

The plasmids, p193 F5F2K(RKKK2) and p193 F5F2K (FLAG) were confirmed to contain the correct inserts through use of PCR analysis and mobility shift assays done on DNA fragments generated by restriction digests of the plasmids. Namely, the relevant portion of the modified loop of the fiber knob present in p193 F5F2K(RKKK2) is set forth in SEQ ID NOs 26 and 27. The relevant portion of the modified loop of the fiber knob present in p193 F5F2K (FLAG) is set forth at SEQ ID NOs: 28 and 29.

These results thus confirm that the methods described herein can be employed to construct transfer vectors encoding fiber sequences having insertions of various peptide motifs in an exposed loop of the knob region of the adenovirus fiber protein.

Example 2

This example describes the construction of adenoviral vectors encoding fiber sequences having insertions of various peptide motifs in a loop of the knob region of the adenovirus fiber protein.

The transfer plasmids p193 F5F2K(RKKK2) and p 193 F5F2K(FLAG) were employed to obtain the corresponding adenoviral vectors comprising the FLAG and RKKK2 peptide motifs. This was accomplished by digesting these plasmids (which contain the essential E4 region of adenovirus) with Sal I, and transfecting them into 293 cells that already had been infected 1 hour earlier with the adenovirus vector AdZ.E4Gus. This adenovirus vector lacks the E4 region and cannot replicate in 293 cells without the E4 genes. Only when AdZ.E4Gus DNA recombines with plasmid DNA such as p193 F5F2K, p193 F5F2K(FLAG), and p193 F5F2K(RKKK2) to obtain the E4 genes is the vector able to replicate in 293 cells. During this recombination to rescue the adenoviral vector, the newly formed vector also picks up the mutated fiber sequence encoded by the plasmids.

Viable recombinant E4+ adenovirus containing the F2K (RKKK2) and F2K(FLAG) DNA sequences (i.e., AdZ-.FLAG and AdZ.RKKK2) were isolated by plaquing the transfected cell lysates 5 days after transfection. The recombinant adenoviruses were then plaque-purified 2 times on 293 cells. The purified plaques were amplified on 293 cells. All viruses were purified from infected cells at 2 days post-infection by 3 freeze-thaw cycles followed by two successive bandings on CsCl gradients. Purified virus was dialyzed into 10 mM Tris, 150 mM NaCl, pH 7.8, containing 10 mM $MgCl_2$, 3% sucrose, and was frozen at −80 until required for use. The purified viruses were verified by PCR to contain either the RKKK2 insert or the FLAG insert.

These adenoviral vectors and the sequences they specifically target due to their possession of modified fiber knobs are depicted in Table 1.

TABLE 1

Adenoviral Vectors Comprising Constrained Peptide Motifs

| Vector Name | Target Receptor | Target Sequence |
|---|---|---|
| AdZ.FLAG | Any receptor (with use of a bispecific antibody) | TRDYKDDDDKTS [SEQ ID NO:23] |
| AdZ.RKKK2 | Heparin sulfate-containing receptors | TRKKKRKKKTS [SEQ ID NO:19] |

These results thus confirm that the methods described herein can be employed to construct adenoviral vectors encoding fiber sequences having insertions of various peptide motifs in an exposed loop of the knob region of the adenovirus fiber protein.

Example 3

This example describes the characterization of adenoviral vectors encoding fiber sequences having insertions of various peptide motifs in a loop of the knob region of the adenovirus fiber protein.

The FLAG insert present in the AdZ.FLAG vector was shown to be functionally accessible and capable of binding the anti-FLAG M2 mAB as assessed by immunofluorescence, as previously described (Wickham et al., 1993). Briefly, 293 cells were infected at a low multiplicity of infection (i.e., about a 0.02 MOI) with the AdZ.RKKK2 or AdZ.FLAG isolates. The cells were fixed at two days post-infection and incubated with either a rabbit anti-penton base polyclonal antibody or a mouse anti-FLAG mAB, followed by incubation with anti-rabbit or anti-mouse FITC antibody. The anti-penton base antibody recognized cells infected by either virus. In comparison, the FLAG mAB recognized only the cells infected with the AdZ.FLAG virus, and not the cells infected with the AdZ.RKKK2 virus.

These results confirm that adenoviruses produced according to the method of the invention are viable, and that the insert (e.g., FLAG epitope) present in an exposed loop of fiber protein is accessible to and capable of binding its corresponding binding entity (e.g., a cell surface binding site or an antibody such as the anti-FLAG antibody). These results confirm that the method of the invention can be employed for adenoviral-mediated cell targeting.

Example 4

This example describes gene delivery mediated by adenoviral vectors encoding fiber sequences having insertions of various peptide motifs in an exposed loop of the knob region of the adenovirus fiber protein.

For testing the ability of the RKKK2 motif to effect cell targeting, 293 cells (which appear to express relatively high levels of the receptor by which wild-type adenovirus fiber protein effects cell entry) were preincubated for 30 minutes in the presence and absence of competing wild-type fiber protein. Purified AdZ or AdZ.RKKK2 vectors were then incubated with the cells for an additional 60 minutes at 37 C. The cells were washed 3 times with PBS, and incubated in culture medium overnight. β-galactosidase activity from lysed cells was then determined using a β-galactosidase fluorometric assay kit (Tropix, Bedford, Mass.). Activity was measured in a luminometer in relative light units (RLU).

Figure 7:
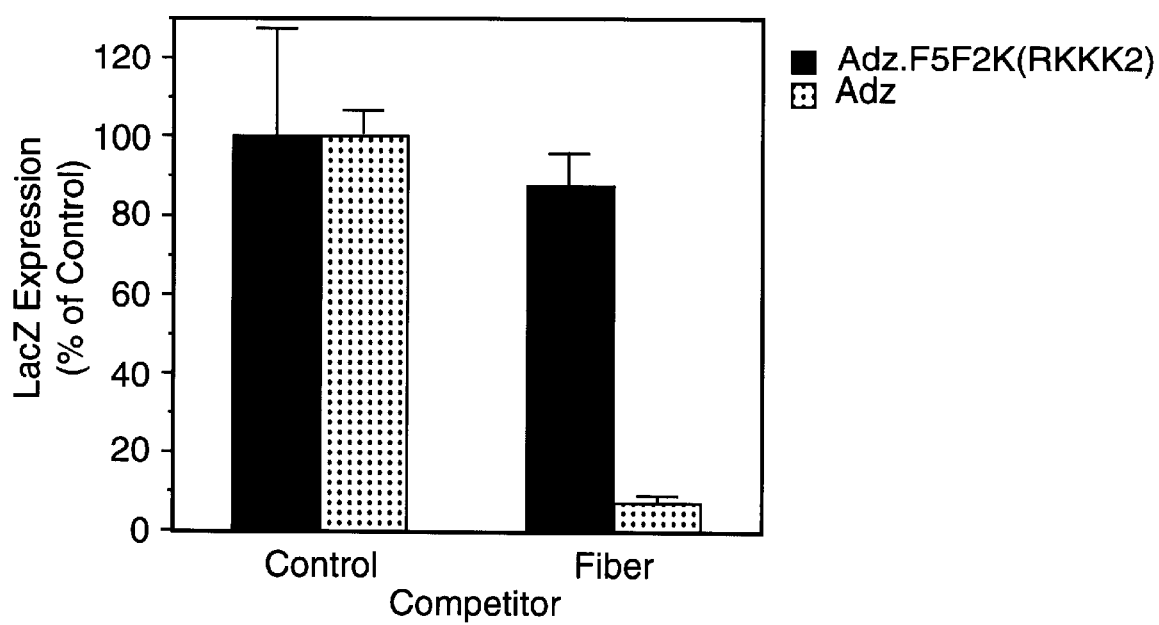
FIG. 7 is a bar graph depicting β-galactosidase expression (% of control) in 293 cells transduced with either AdZ.F5F2K(RKKK2) (closed bars) or AdZ (open bars) in the absence (control) or presence (fiber) of soluble fiber protein.
Figure 8:
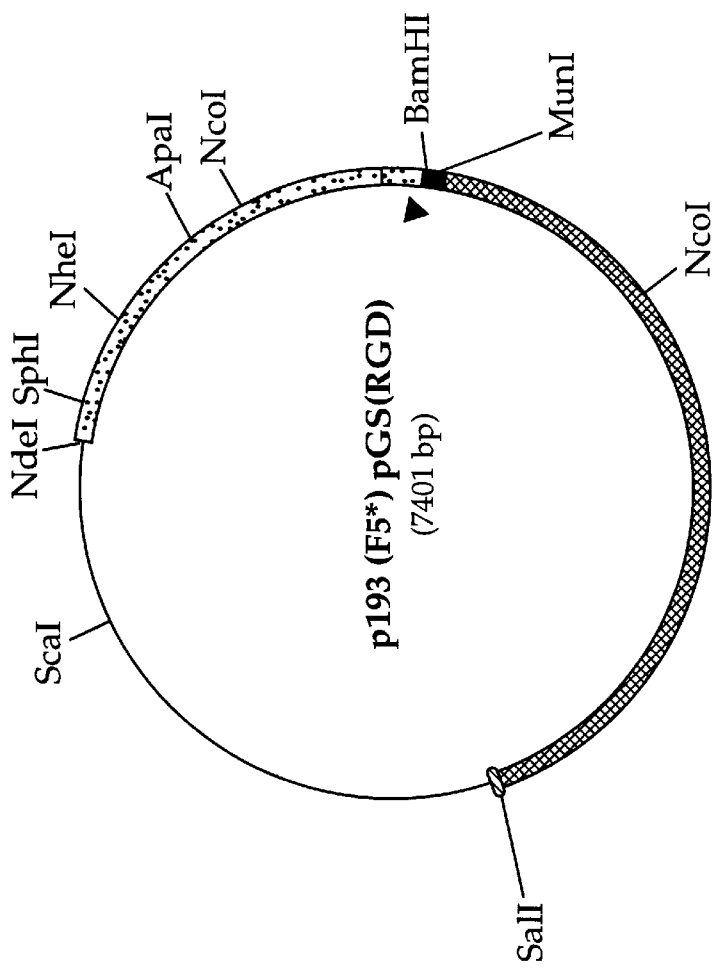
FIG. 8 depicts the transfer plasmid p193(F5)RGD, which was used to create the adenovirus vector AdZ.RGD.

The data illustrated in FIG. 7 demonstrates gene delivery to 293 cells effected by the AdZ.RKKK2 vector. As can be seen from this figure, recombinant wild-type fiber protein blocked gene delivery by AdZ, but not by AdZ.RKKK2. The AdZ.RKKK2 vector was able to overcome the fiber-mediated block to adenoviral-mediated gene delivery.

These results confirm that this constrained peptide motif present in the fiber loop is able to efficiently mediate cell binding/entry. Moreover, the results further confirm that adenoviral vectors encoding fiber sequences having insertions of various peptide motifs in an exposed loop of the knob of the adenovirus fiber protein can be employed for delivery (e.g., of DNA and/or protein) to cells.

Example 5

This example describes other oligonucleotides that can be employed for inserting a nonnative amino acid sequence into a chimeric adenovirus fiber protein, preferably in an exposed loop of the adenovirus fiber knob, but also at the C-terminus of the protein.

The cloning techniques described in the previous example can be employed to incorporate into an exposed loop of the fiber knob inserts comprising peptide motifs that will target, for instance, $\alpha_v$ integrins, $\alpha_5\beta_1$ integrin, FLAG mAb, or other cell surface binding sites. In particular, an HAαv sequence (e.g., comprising SEQ ID NOs: 30 and 31) can be inserted. For example, the sequence can be inserted with use of the 39-mer sense oligonucleotides HAαv(s) (comprising SEQ ID NO:32) and HAαv(a) (comprising SEQ ID NO:33). These oligonucleotides were used to make p193(F5*)pGS (RGD), which was used to make AdZ.RGD.

Similarly, an HAα5β1 sequence (e.g., SEQ ID NOs: 34 and 35) can be inserted for targeting integrin α5γ1. The sequence can be inserted with use of the 39-mer sense oligonucleotides HAα5β1(s) (comprising SEQ ID NO:36) and HAα5β1(a) comprising SEQ ID NO:37).

These sequences (and other sequences described herein) that allow targeting to he $\alpha_v$ integrins are of use since this target receptor demonstrates broad distribution, including to endothelial cells and smooth muscle cells. The adhesion receptor appears to be important in wounds (i.e., both healing and exacerbation thereof), as well as in angiogenesis, restenosis and metastasis. Generally, the receptor is upregulated in proliferating endothelial cells and smooth muscle cells, and exhibits high expression in melanoma and glioma. Normal ligands for the av integrins receptor include vitronectin, collagen, fibronectin, laminin, and osteopontin.

Also, an E-selectin targeting sequence (e.g., comprising SEQ ID NOs: 38 and 39) can be inserted. The E-selectin sequence can be inserted with use of the 42-mer sense oligonucleotide E-selectin(s) (comprising SEQ ID NO:40) and the 42-mer antisense oligonucleotide E-selectin(a) (comprising SEQ ID NO:41). Further ligands that bind elastin have been described in the art and similarly can be employed as nonnative amino acid sequences for the generation of peptide motifs as described herein (see, e.g., Martens et al., *J Biolog. Chem.*, 270, 21129–21136 (1995)).

Furthermore, a PolyGS(RKKK)3 sequence (e.g., SEQ ID NOs: 42 and 43), or other variations of this sequence, can be inserted. The sequence can be inserted with use of the 39-mer sense oligonucleotide PolyGS(RKKK)$_3$(s) (comprising SEQ ID NO:44) and the 39-mer antisense oligonucleotide PolyGS(RKKK)$_3$(a) (comprising SEQ ID NO:45).

This example thus confirms that other oligonucleotides can be employed for inserting a nonnative amino acid sequence into a fiber protein. Such insertions can either be made in an exposed loop of the adenovirus fiber knob or, as described as follows, at the C-terminus of the fiber protein.

Moreover, the nonnative amino acid sequence can be incorporated into the chimeric fiber protein not merely as an insertion into the sequence, but also as a replacement of adenoviral sequences. This can be done through modification of the cloning procedures described herein, as are known to those skilled in the art.

Example 6

In a similar fashion to the constraint achieved by placing a peptide motif within an exposed loop of the adenovirus fiber protein, constraint can be obtained through appropriate modification of a peptide motif at the C-terminus of the fiber protein to create, in essence, a nonpreexisting loop at this site. Thus, this example describes the construction of transfer vectors encoding fiber sequences having insertions of various constrained peptide motifs at the C-terminus of the adenovirus fiber protein. This method is depicted in FIG. 2.

The transfer vector p193(F5*) described in Example 1 was used as a base plasmid to create chimeric adenovirus particles containing C-terminal additions to the fiber gene. In particular, DNA sequences encoding a linker sequence followed by a targeting sequence and a stop codon were cloned into the Bam HI site to create further transfer vectors which, in turn (i.e., via the construction of the further transfer vectors p193(F5)pGS(RGD) and p193(F5)pGS) were used to make chimeric adenovirus particles.

The mutant transfer plasmids containing sequences encoding an amino acid glycine/serine repeat linker, a targeting sequence, and a stop codon were made by cloning synthetic oligonucleotides into the Bam HI site of p193 (F5*). The cloning reactions essentially were carried out as described in Example 1. In particular, the overlapping synthetic oligonucleotides used to make the transfer plasmid p193(F5)pGS(RGD) depicted in FIG. 8 were: sense, SEQ ID NO:46; antisense, SEQ ID NO:47. This plasmid comprises SEQ ID NO:48, encoding the amino acid sequence SEQ ID NO:49. The RGD peptide is present within this larger sequence. The plasmid p193(F5)pGS(RGD) thus comprises the targeting sequence CDCRGDCFC [SEQ ID NO:3] which is present in the larger sequence SEQ ID NO:86. This sequence, like other sequences described earlier containing the tripeptide motif RGD, acts as a ligand for the target receptor $\alpha_5$ integrins. However, highly constrained forms of RGD bind with higher affinities to integrins than linear forms (see, e.g., Aumailley et al., FEBS, 291, 50–54 (1991); Cardarelli et al., *J. Biolog. Chem.*, 269., 18668–18673 (1994); Koivunen et al., *Bio/Technology*, 13, 265–270 (1995)). Along these lines, the constrained RGD targeting motif present in p193(F5)pGS(RGD) binds with about 100-fold higher affinity to $\alpha_v$ integrins than does similar linear RGD motifs. Each pair of cysteines on either side of the RGD form disulfide binds with the opposite pair of cysteines to form a highly constrained RGD loop.

Moreover, variations of the CDCRGDCFC [SEQ ID NO:3] targeting sequence can be employed in the context of the present invention. For instance, instead of two cysteine residues on either side of the RGD tripeptide sequence, only one residue can be used instead. Any sequence can be employed, so long as a loop-like structure is created encompassing the RGD sequence, and so long as the sequence comprises one or more cysteine pairs. Moreover, the RGD sequence can be substituted by another sequence, e.g., LDV.

In terms of construction of the related transfer plasmid pl 93(F5)pGS, the overlapping synthetic oligonucleotides used to make the transfer plasmid were: sense, PolyGS(s), [SEQ ID NO:50]; antisense, PolyGS (a), [SEQ ID NO:51]. The sense and antisense oligonucleotides were mixed in equimolar ratios and cloned into the Bam HI site of p193(F5*) to create p193(F5)pGS. The transfer vector p193(F5)pGS then was used to construct further transfer vectors, as described in the following Examples.

Thus, this example confirms that transfer vectors encoding fiber sequences having insertions of various constrained peptide motifs at the C-terminus of the adenovirus fiber protein can be constructed according to the invention. Other transfer vectors (i.e., having different targeting sequences) also can be constructed using this approach.

Example 7

This example describes the construction of adenovirus vectors encoding fiber sequences having insertions of various constrained peptide motifs at the C-terminus of the adenovirus fiber protein.

The E1- and E3-deleted adenovirus AdZ employed for these experiments contains the β-galactosidase gene under the control of a cytomegalovirus (CMV) promoter and integrated into the adenoviral genome. AdZ was propagated in human embryonic kidney 293 cells, which contain the complementary E1 region for virus growth. ADZ.RGD (as well as other vectors targeted to other adhesion receptors described herein) was derived directly from AdZ. These viruses likewise are E1- and E3-deleted, and are identical to AdZ, except for the presence of additional amino acids on the C-terminus of the fiber proteins.

The transfer plasmids, p193(F5)pGS and p193(F5)pGS (RGD), which contain the essential E4 region of adenovirus, were employed for adenoviral vector construction. These transfer plasmids were cut with Sal I and transfected into 293 cells that had been infected one hour prior with the adenovirus vector, AdZ.E4Gus. The adenovirus vector AdZ.E4Gus lacks the E4 region and cannot replicate in 293 cells without the E4 genes. Only when AdZ.E4Gus DNA recombines with the p193(F5)pGS or p193(F5)pGS(RGD) plasmid DNA to obtain the E4 genes is the vector able to replicate in 293 cells. During this recombination, the newly formed vector also picks up the fiber mutations encoded in the plasmids. Viable recombinant E4+ adenovirus containing the pGS and pGS(RGD) mutations were then isolated by plaquing the transfected cell lysates 5 days after transfection. Their resultant vectors, AdZ.pGS and ADZ.RGD, were isolated and purified by two successive rounds of plaquing on 293 cells. Each vector was verified to contain the correct insert by sequencing PCR products from virus DNA that spans the region of the insert DNA.

This example confirms that adenovirus vectors encoding fiber sequences having insertions of various constrained peptide motifs at the C-terminus of the adenovirus fiber protein can be constructed according to the invention.

Example 8

This example describes the construction of transfer vectors and adenoviral vectors with use of other oligonucleotides that can be employed for inserting a nonnative amino acid sequence into a chimeric adenovirus fiber protein, preferably in an exposed loop of the adenovirus fiber knob, but also at the C-terminus of the protein.

The cloning techniques described in Example 6 were employed to create additions at the C-terminus. Basically the transfer vectors described in this Example (in particular, the transfer vector p193(F5)pGS) were linearized at the unique cloning site Spe I present in the vectors, and new sequences were inserted at this site. Other means (e.g., PCR reactions) also can be employed to make insertions into this unique site. Similarly, the cloning techniques described in Example 5 can be employed to incorporate into an exposed loop of the fiber knob inserts comprising peptide motifs that target other cell surface binding sites or epitopes for an antibody.

In particular, multiple copies of the RGD sequence (i.e., a polyRGD or pRGD sequence; SEQ ID NOs: 52 and 53) were inserted. The sequence was inserted with use of the sense oligonucleotide pRGDs (comprising SEQ ID NO:54) and the antisense oligonucleotide pRGDa (comprising SEQ ID NO:55). The resultant plasmid p193(F5*)RGD was employed to create the adenovirus AdZ.pRGD. A comparison of the inserts present in ADZ.RGD and AdZ.pRGD (with the RGD peptide indicated emboldened) is presented in Table 2.

TABLE 2

Comparison of Adenoviral Vectors AdZ.RGD and AdZ.pRGD

| Vector Name | Target Receptor | Target Sequence |
| --- | --- | --- |
| AdZ.RGD | α$_v$ Integrins | SACDCRGDCFCGTS [SEQ ID NO:68] |
| AdZ.pRGD | α$_v$ Integrins β$_1$ Integrins | TS(GRGDTF)$_3$SS [SEQ ID NO:52] |

Similarly, one or more copies of an LDV targeting sequence can be inserted. The LDV target receptor is distributed in hematopoietic cells, lymphocytes, and monocytes/macrophages. The adhesion receptor is highly expressed on resting lymphocytes involved in cell-matrix and cell-cell interactions (e.g., during hematopoietic extravasation, as well as inflammation, and lymphocyte trafficking). Ligands for the α$_4$ integrins target receptor include, but are not limited to, fibronectin (an extracellular matrix protein), VCAM-1 (which targets endothelial tissue), and MAdCAM (α$_4$β$_7$)(which is gut-specific). In particular, the α$_4$ integrins targeting sequences includes the sequence EILDVPST ([SEQ ID NO:56] encompassed by the sequence above, and the sequence (EILDVPS)$_3$ [SEQ ID NO:57].

In particular, multiple copies of the LDV sequence (i.e., a polyLDV or pLDV sequence) can be inserted to comprise SEQ ID NOs:58 and 59. This sequence was inserted with use of the sense oligonucleotide pLDVs (comprising SEQ ID NO:60) and the antisense oligonucleotide pLDVa (comprising the sequence SEQ ID NO:61).

Figure 9:
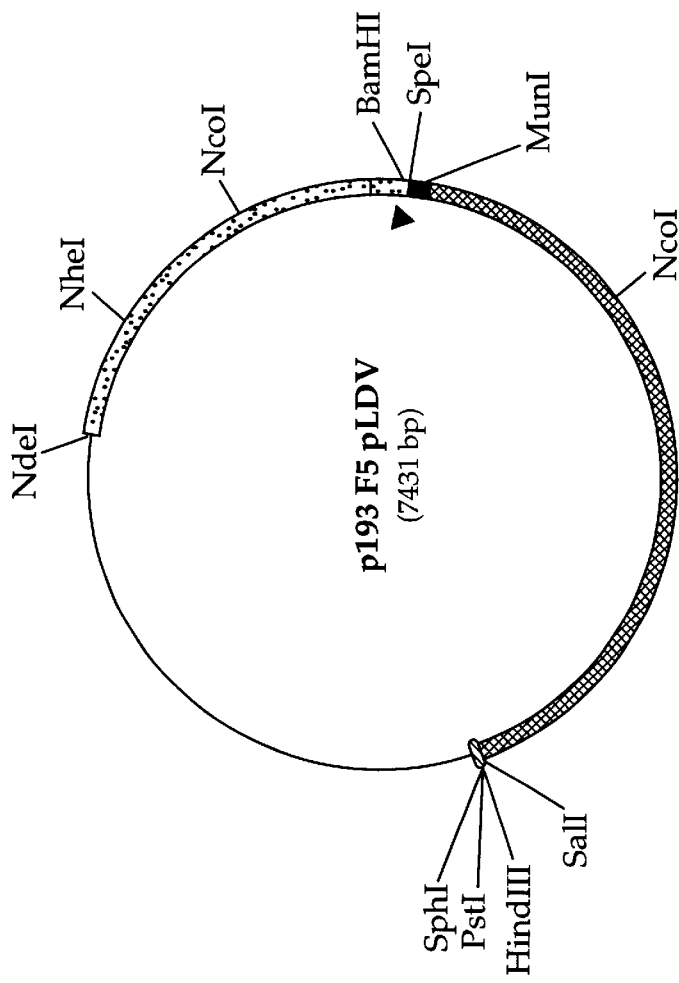
FIG. 9 depicts the transfer plasmid p193(F5)pLDV, which was used to create the adenovirus vector AdZ.pLDV.

Such insertion resulted in the generation of the vector p 193(F5)pLDV depicted in FIG. 9. The LDV targeting motif present in this vector (i.e., comprising the sequence of SEQ ID NO:59) binds with sub-millimolar affinity to α$_4$ integrins. The LDV motif is repeated 3 times in each fiber monomer for a total of 9 motifs per fiber molecule. This vector further was employed for the generation of a corresponding adenoviral vector.

Figure 10:
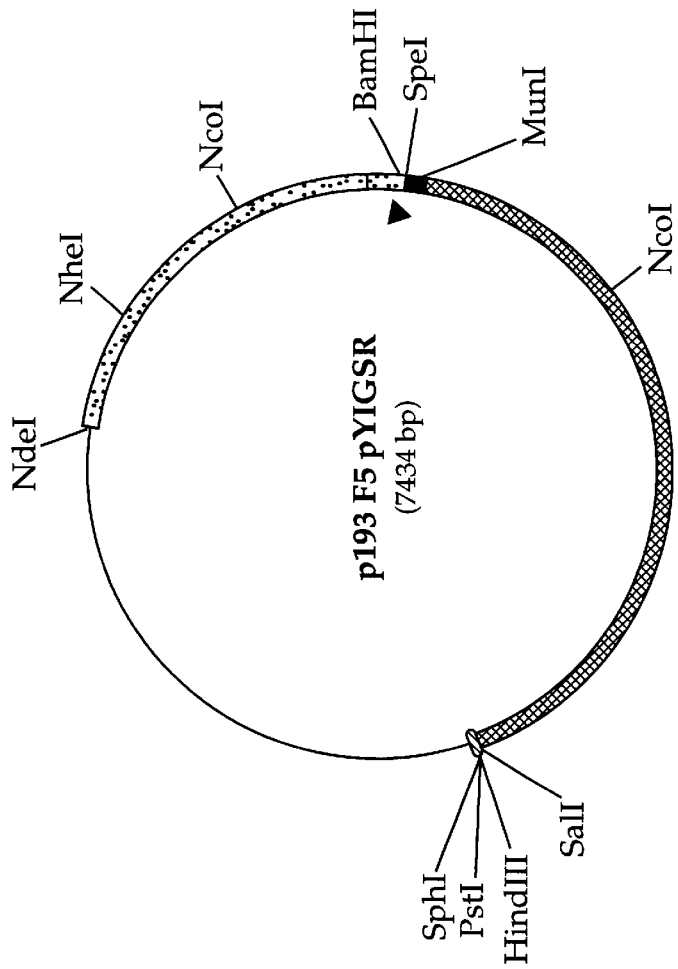
FIG. 10 depicts the transfer plasmid p193(F5) pYIGSR, which was used to create the adenovirus vector AdZ.pYIGSR.

Furthermore, a pYIGSR targeting sequence was inserted at the C-terminus of the fiber protein to derive the plasmid p193(F5)pYIGSR depicted in FIG. 10. The fiber protein in this plasmid comprises SEQ ID NOs: 62 and 63. The sequence was inserted with use of the sense oligonucleotide pYIGSRs (comprising SEQ ID NO:64) and the antisense oligonucleotide pYIGSRa (comprising SEQ ID NO:65).

The resultant plasmid contains the YIGSR [SEQ ID NO:66] targeting motif, which binds with sub-millimolar affinity to the high affinity laminin receptor. The motif, present as YIGSRG (SEQ ID NO:67), is repeated 3 times in each fiber monomer for a total of 9 motifs per fiber molecule. In particular, the motif provides for targeting to the 67 kilodalton laminin/elastin receptor. This receptor is present in monocytes/neutrophils, vascular smooth muscle, fibroblasts, and chondrocytes, and is upregulated in multiple tumors. Furthermore, the receptor appears to be involved in tumor metastasis and angiogenesis. Typical ligands for the laminin/elastin receptor include laminin, elastin, and galactose. The p193(F5)pYIGSR plasmid derived herein further was employed to create the adenovirus vector AdZ.pYIGSR.

This example thus confirms that other oligonucleotides can be employed for inserting a nonnative amino acid sequence into a fiber protein. Such insertions can either be made in an exposed loop of the adenovirus fiber knob, or, as described as follows, at the C-terminus of the fiber protein. Moreover, the nonnative amino acid sequence can be incorporated into the chimeric fiber protein not merely as an insertion into the sequence, but also, as a replacement of adenoviral sequences. This can be done through simple modification of the cloning procedures described herein, such as are known to those skilled in the art.

Example 9

This example describes the characterization of adenoviral vectors encoding fiber sequences having an insertion of a constrained RGD peptide motif at the C-terminus of the adenovirus fiber protein. In particular, the ability of these vectors to produce active virus particles in different cells was investigated.

For the Western analysis of virus particles, purified virus particles ($2 \times 10^{10}$) in a volume of 10 µl were diluted 1:1 in Laemmli running buffer and loaded onto a 9% acrylamide, 0.1% SDS gel. The gel was run at 150 mV and was then transferred to nitrocellulose. The nitrocellulose was blocked with 5% dry milk and probed with a combination of rabbit polyclonal antibodies directed against denatured Ad5 virions (1:1000) and against fiber protein (1:5000). The proteins were detected using antirabbit-peroxidase (1:5000) and a commercially available chemiluminescent detection kit.

The fiber proteins of the recombinant adenoviruses AdZ-.pGS and ADZ.RGD were shifted upward on the Western relative to the fiber protein contained by the AdZ vector. A gel run in parallel that was transferred to nitrocellulose and probed using only the polyclonal antibody directed against the fiber protein demonstrated that the shifted bands in the Western analysis were, in fact, fiber protein. These results confirm that the AdZ.pGS and ADZ.RGD fiber proteins contain the appropriate amino acid inserts.

The viral production kinetics were determined to confirm that viable adenovirus was being produced in 293 cells infected with various adenoviral vectors according to the invention. To carry out these studies, radiolabeled adenovirus was made by adding 50 µCi/ml [$^3$H]thymidine (Amersham, Arlington Heights, Ill.) to the medium of infected cells at 20 hours following their infection at an MOI of 5. The infected cells were then harvested at 60 hours post-infection, and the virus was purified as previously described. The activity of the labeled viruses was approximately $10^4$ virus particles/cpm. Infectious particles were titered in fluorescence focus units (ffu) using a fluorescent focus assay on 293 cells.

Figure 11:
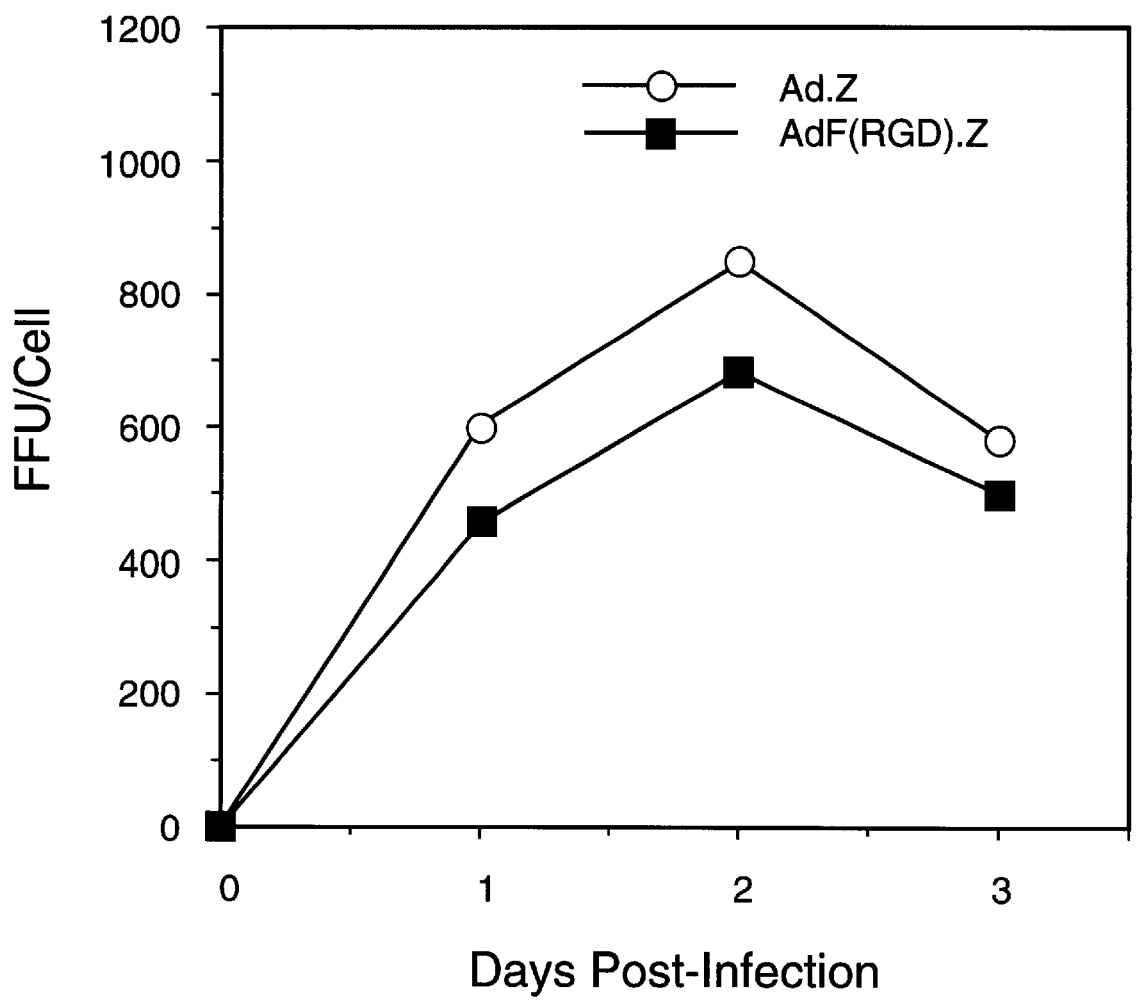
FIG. 11 is a graph of days post-infection versus FFU/cell for 293 cells infected with AdZ (open circles) or AdZ.RGD (closed squares).

Active virus particle production kinetics from infected 293 cells were determined by infecting $10^6$ 293 cells with 0.2 ml of either AdZ or ADZ.RGD for 1 hour in 6 cm plates at an MOI of 10 on day 0. The cells were harvested on 1, 2, and 3 days post-infection. The cells were spun down and resuspended in 1 ml of PBS for AdZ and ADZ.RGD. The cells were frozen and thawed 3 times to release the virus particles. The lysates were then assayed for the number of active particles produced per cell using standard techniques. The results of these experiments (depicted in FIG. 11) confirm that the modifications to the fiber protein in ADZ.RGD do not significantly affect the production of active virus particles compared to the unmodified vector, AdZ.

The particle dose-response of the vectors AdZ and ADZ.RGD on A549 epithelial, CPAE endothelial, and human intestinal smooth muscle (HISM) cells similarly was investigated. HISMC, CPAE, or A549 cells ($5 \times 10^5$ cells/well) were seeded onto 6 cm plates 1–2 days prior to experiments. In assays evaluating the vector dose-response in fiber receptor-expressing cells, increasing concentrations of AdZ or AdZ.RGD particles were incubated with the cells for 60 minutes at 37 C. in 0.2 ml DMEM +20 mM HEPES. The plates were shaken every 10 minutes during this incubation. The cells were then washed 2 times with DMEM and cultured in DMEM +5% calf serum for 2–3 days at 37 C. The medium was than aspirated, and the cells were lysed in 1 ml 1× reporter lysis buffer +10 mM EDTA (Promega, Madison, Wis.). The β-galactosidase activity in the cell lysates was then assayed as previously described. Results are the average of duplicate measurements.

Figure 12:
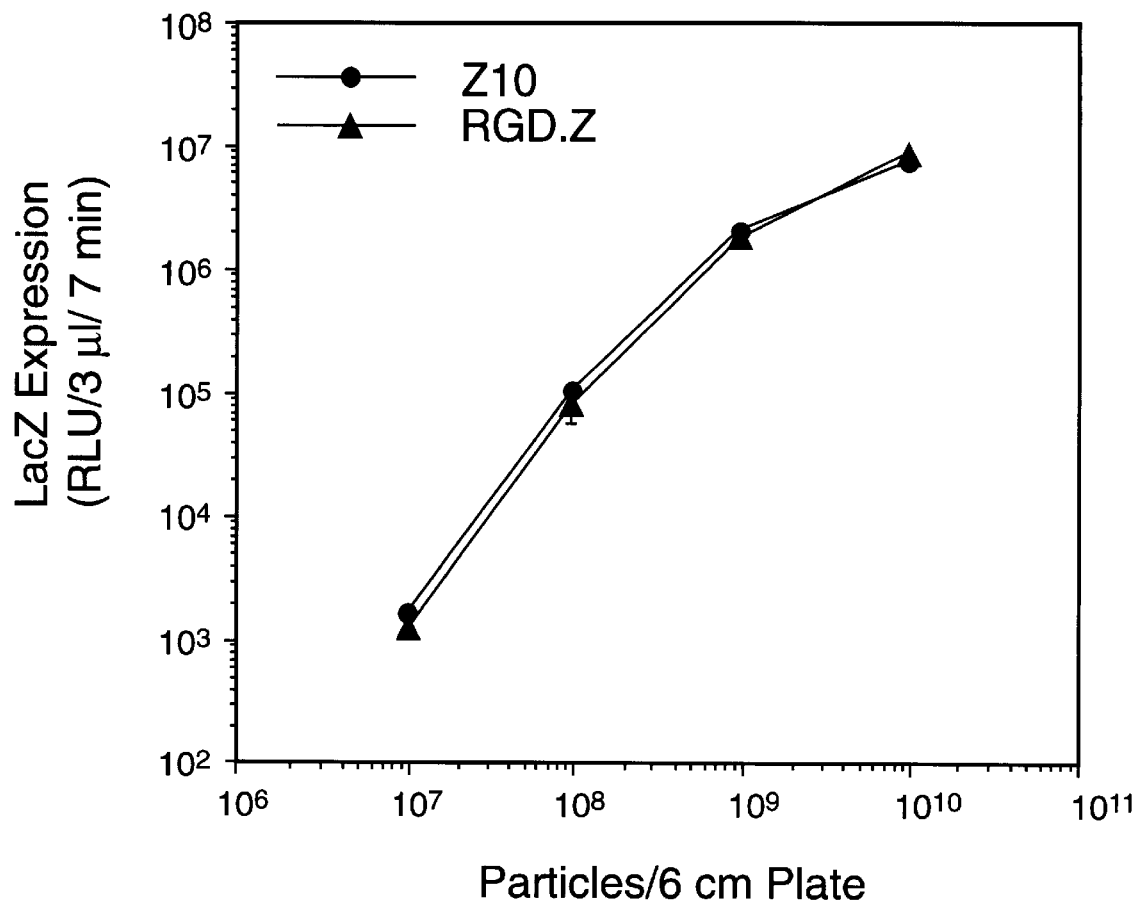
FIG. 12 is a graph of virus particles added (per 6 cm plate) versus β-galactosidase expression (RLU/0.3 μl/7 minutes) for A549 cells infected with AdZ (closed circles) or AdZ.RGD (closed triangles).
Figure 13:
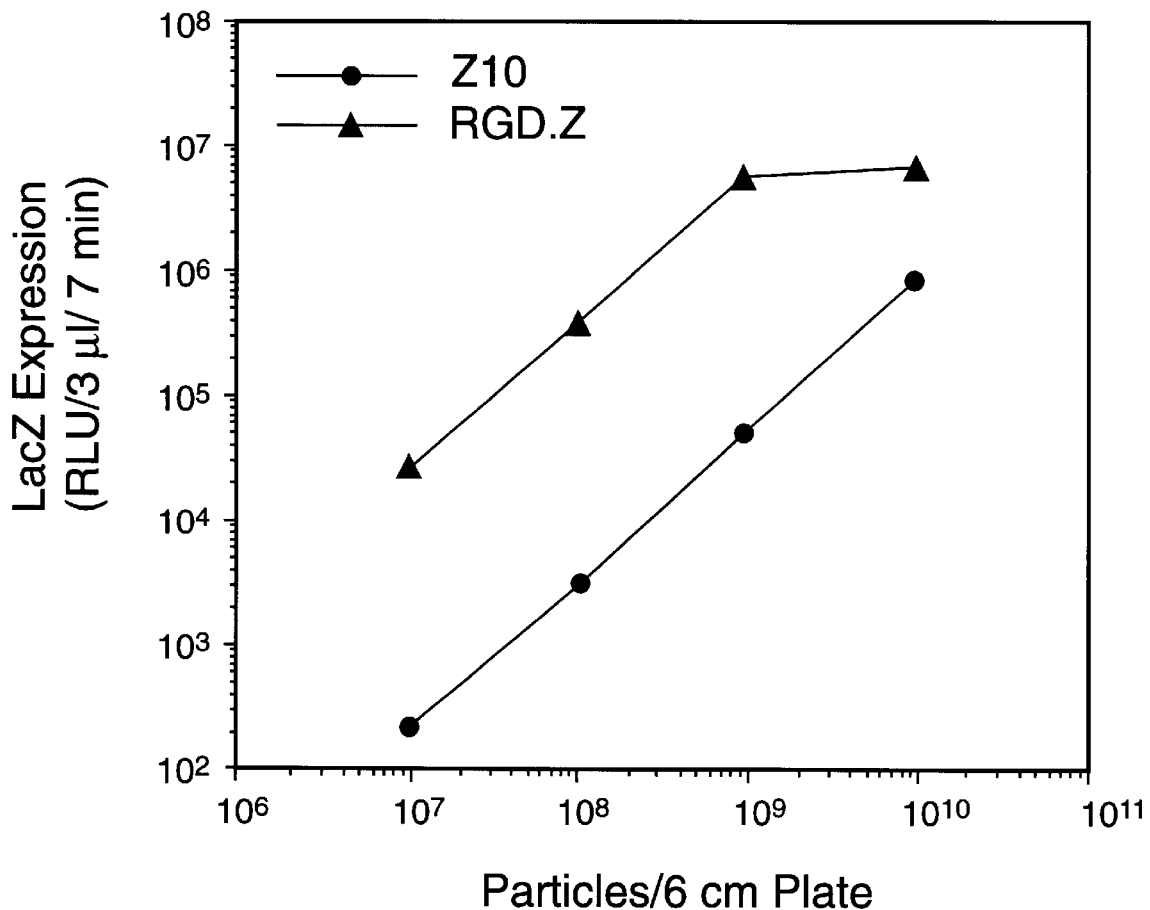
FIG. 13 is a graph of virus particles added (per 6 cm plate) versus β-galactosidase expression (RLU/0.3 μl/7 minutes) for CPAE cells infected with AdZ (closed circles) or AdZ.RGD (closed triangles).
Figure 14:
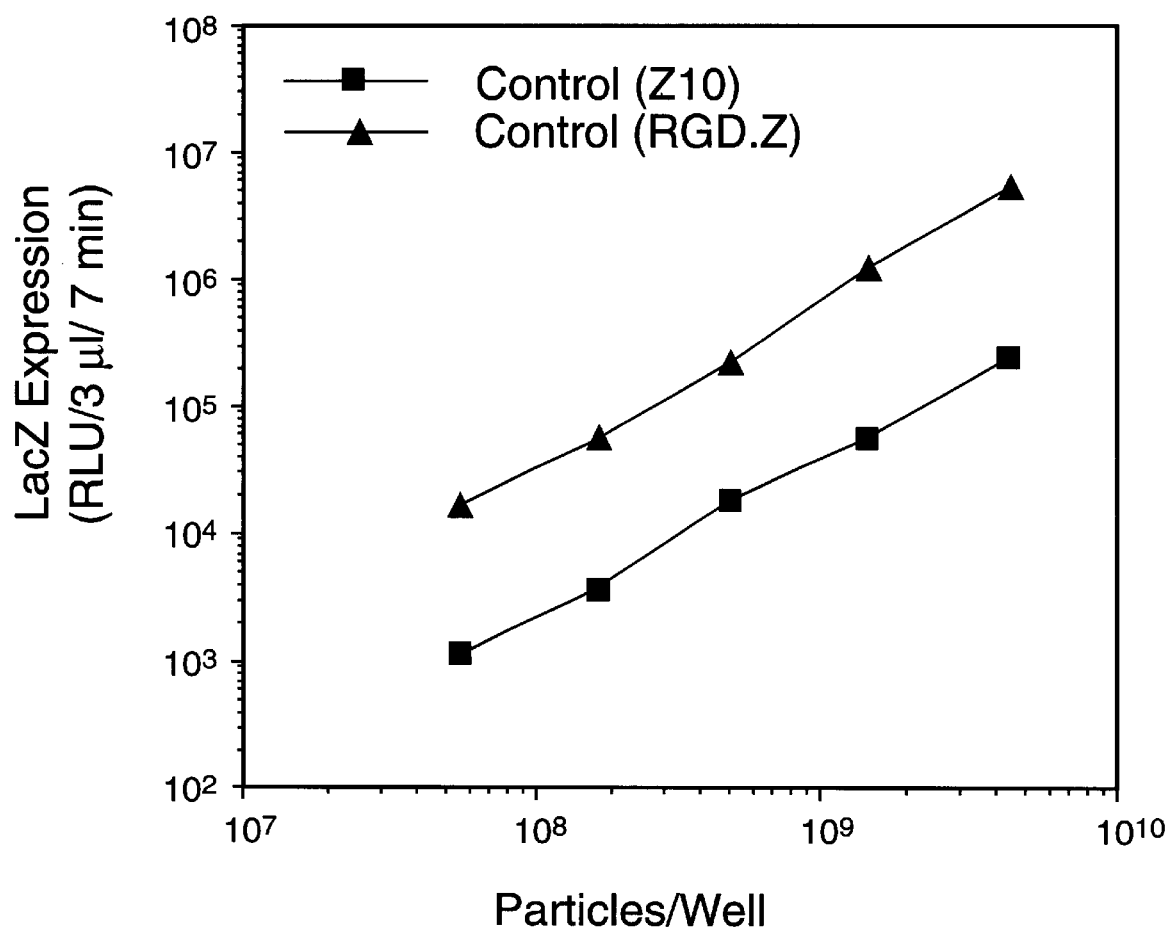
FIG. 14 is a graph of virus particles added (per 6 cm plate) versus β-galactosidase expression (RLU/0.3 μl/7 minutes) for HISM cells infected with AdZ (closed circles) or AdZ.RGD (closed triangles).

The results of these experiments are presented in FIGS. 12–14. These experiments confirm that the AdZ and ADZ.RGD vectors are equivalent in terms of their ability to enter and produce viable virus particles in cells (A549) known to express high levels of adenovirus fiber receptor (i.e., A549 cells as presented in FIG. 12). However, for the CPAE and HISM cells (i.e., presented in FIG. 13 and FIG. 14, respectively) which lack significant levels of adenovirus fiber receptor, but do express $\alpha_v$ integrins, the AdZ.RGD vector is much more efficient in transduction than is the unmodified, AdZ vector. Transduction of the CPAE and HISM cells by ADZ.RGD is roughly 100-fold and 30-fold higher, respectively, than AdZ over a wide range of vector concentrations.

These results validate that amino acid inserts present in adenoviral vectors according to the invention are appropriately translated within the context of the chimeric adenovirus fiber protein, and that the resultant chimeric fiber protein is functional, as assessed by the generation of viable adenoviruses containing this protein. Moreover, the results confirm that the peptide motif present in the chimeric fiber protein is able to redirect adenovirus binding, and to selectively effect adenoviral cell binding/entry with a high efficiency.

Example 10

This example describes the binding behavior of adenoviral vectors encoding fiber sequences having an insertion of a various constrained peptide motif at the C-terminus of the adenovirus fiber protein.

Figure 15:
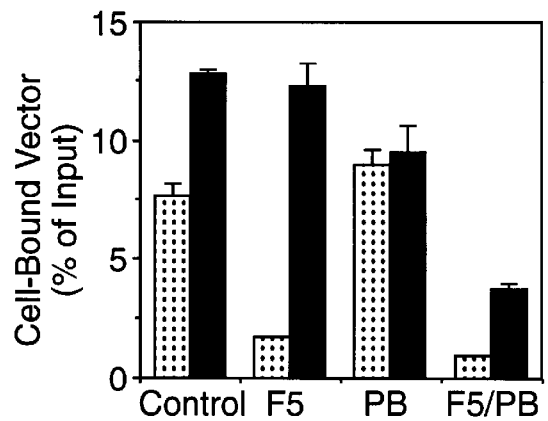
FIG. 15 is a bar graph depicting the binding of AdZ.RGD (closed bars) and AdZ (open bars) expressed as % of input of cell-bound vector in 835 kidney cells in either the absence (control) or presence of competing fiber protein (F5), penton base protein (PB), or both fiber and penton base protein (F5/PB).
Figure 16:
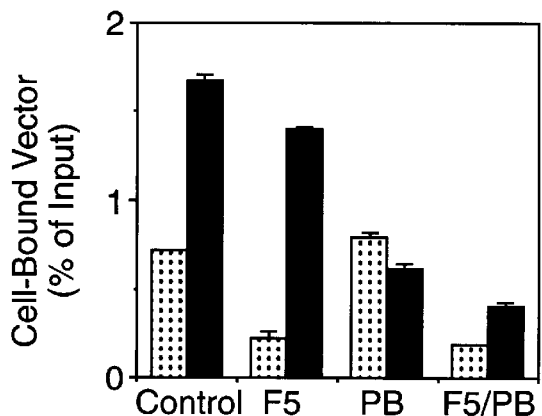
FIG. 16 is a bar graph depicting the binding of AdZ.RGD (closed bars) and AdZ (open bars) expressed as % of input of cell-bound vector in A10 smooth muscle cells in either the absence (control) or presence of competing fiber protein (F5), penton base protein (PB), or both fiber and penton base protein (F5/PB).
Figure 17:
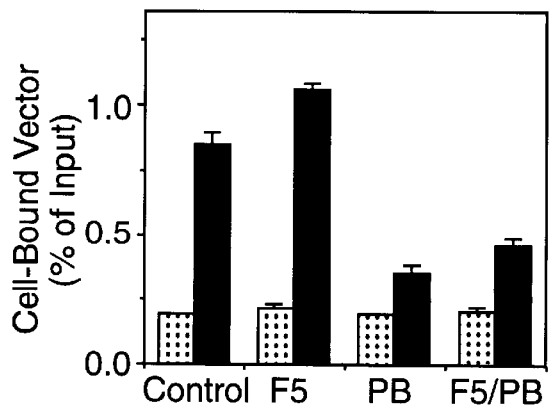
FIG. 17 is a bar graph depicting the binding of AdZ.RGD (closed bars) and AdZ (open bars) expressed as % of input of cell-bound vector in CPAE endothelial cells in either the absence (control) or presence of competing fiber protein (F5), penton base protein (PB), or both fiber and penton base protein (F5/PB).

The specificity of the AdZ and the AdZ.RGD vectors in binding to kidney (835), smooth muscle (A10), and endothelial (CPAE) cells was studied. For these experiments, monolayers of 835, A10, or CPAE cells in 24 well tissue culture plates were preincubated for 45 minutes with 0.3 ml medium containing soluble recombinant fiber (F5; 3 ug/ml), penton base (PB; 50 µg/ml), fiber plus penton base, or neither coat protein. Radiolabeled AdZ or AdZ.RGD was then added to the wells and incubated for 90 minutes while rocking at room temperature. The wells were washed 3 times with PBS, and the remaining cell-associated radioactivity was determined in a scintillation counter. The results of these experiments are presented graphically in FIGS. 15–17, and quantitatively in Table 3.

TABLE 3

Comparison of AdZ and AdZ.RGD binding to three cell lines*

|  | 835 HEK** | | CPAE** | | A10** | |
| --- | --- | --- | --- | --- | --- | --- |
|  | AdZ | AdZ.RGD | AdZ | AdZ.RGD | AdZ | AdZ.RGD |
| Control | 7.6 | 12.7 | 0.19 | 0.84 | 0.72 | 1.68 |
| Fiber | 1.7 | 12.3 | 0.22 | 1.06 | 0.23 | 1.40 |
| PB | 9.0 | 9.7 | 0.20 | 0.37 | 0.80 | 0.62 |
| Fiber/PB | 1.0 | 3.7 | 0.21 | 0.46 | 0.20 | 0.41 |

*Values represent percentage of input vector in binding assay.
**Error for all values less than 10%.

These results confirm that fiber protein significantly blocks AdZ transduction, but not AdZ.RGD transduction of both the 835 (FIG. 15) and A10 (FIG. 16) cells. Only fiber plus penton base, which, in combination, blocks both fiber receptor and $\alpha_v$ integrins, is able to significantly block binding of AdZ.RGD to these cells. For the CPAE cells which lack detectable levels of fiber receptor (FIG. 17) penton base alone is able to significantly block binding of AdZ.RGD.

These results demonstrate that ADZ.RGD interacts with $\alpha_v$ integrins on cells. Moreover, the results validate that the peptide motif as present in the fiber protein of ADZ.RGD can effectively be employed to target adenovirus to particular cells.

Example 11

This example describes gene delivery mediated by adenoviral vectors encoding insertions of various sequences at the C-terminus of the adenovirus fiber protein.

For testing the ability of the YIGSR peptide motif to effect cell targeting, A549 cells were preincubated for 30 minutes in the presence and absence of competing wild-type fiber protein. Purified AdZ or AdZ.pYIGSR vectors were then incubated with the cells for an additional 60 minutes at 37 C. The cells were then washed 3 times with PBS and incubated in culture medium overnight. β-galactosidase activity from the lysed cells was determined.

Figure 18:
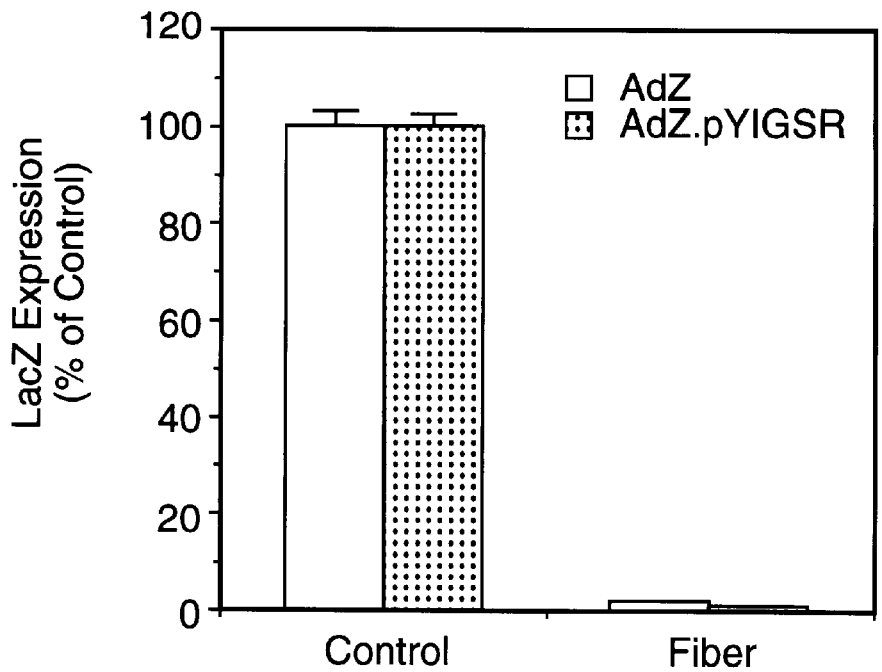
FIG. 18 is a bar graph depicting β-galactosidase expression (% of control) in A549 cells transduced with either AdZ.pYIGSR (closed bars) or AdZ (open bars) in the absence (control) or presence (fiber) of soluble fiber protein.

As presented in FIG. 18, recombinant wild-type fiber protein completely blocked gene delivery by both vectors. Increased gene delivery by the AdZ.pYIGSR vector is not observed in the presence of fiber protein. This indicates that the pYIGSR targeting motif is not of sufficiently high affinity to overcome the block to adenovirus binding that is achieved with the addition of soluble fiber protein.

For testing the ability of the pLDV motif to effect cell targeting, Ramos cells (which express high levels of the $\alpha_4$ integrin target receptor) were preincubated for 30 minutes in the presence and absence of competing wild-type fiber protein. The purified AdZ or AdZ.pLDV vectors were then incubated with the cells for an additional 60 minutes at 37 ° C. The cells were washed 3 times with PBS, and incubated in culture medium overnight. β-galactosidase activity from the lysed cells was then determined.

Figure 19:
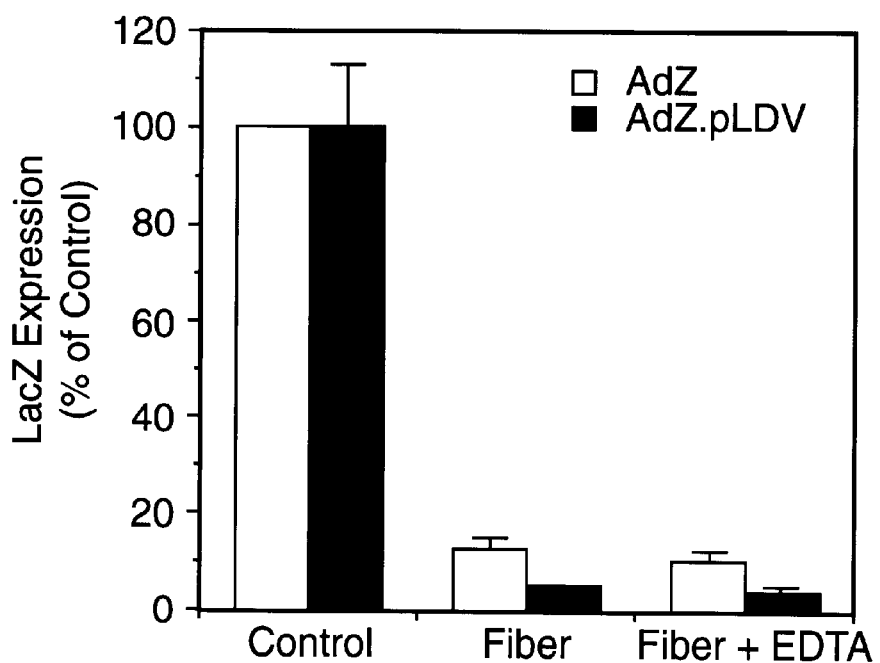
FIG. 19 is a bar graph depicting β-galactosidase expression (% of control) in Ramos cells transduced with either AdZ.pLDV (closed bars) or Adz (open bars) in the absence (control) or presence (fiber) of soluble fiber protein, or fiber protein and EDTA (fiber+EDTA).

FIG. 19 illustrates gene delivery to Ramos cells effected by the AdZ.pLDV vector. As can be seen from this figure, recombinant wild-type fiber protein blocked gene delivery by both AdZ and AdZ.pLDV. As with AdZ.pYIGSR, there is no evidence of increased gene delivery effected by the AdZ.pLDV vector in the presence of fiber protein. This indicates that the pLDV targeting motif, like the YIGSR targeting motif, is not of sufficiently high affinity to overcome the fiber-mediated block to protein binding. The remaining gene delivery capacity of AdZ.pLDV that is not blocked by the addition of soluble fiber protein also is not blocked by further incubation with EDTA. In comparison, the interaction of the $\alpha_4$ integrins with the LDV motif normally present in fibronectin is blocked by EDTA. This result further confirms that the pLDV targeting motif is not interacting with high enough affinity with $\alpha_4$ integrins to increase vector binding and gene delivery to the Ramos cells. However, with both the YIGSR motif (i.e., comprising the sequence of [SEQ ID NO:66] and the LDV motif, it is possible that high affinity peptide motifs could be derived by the conformational restraint of these peptides in an exposed loop of the fiber proteins.

Figure 20:
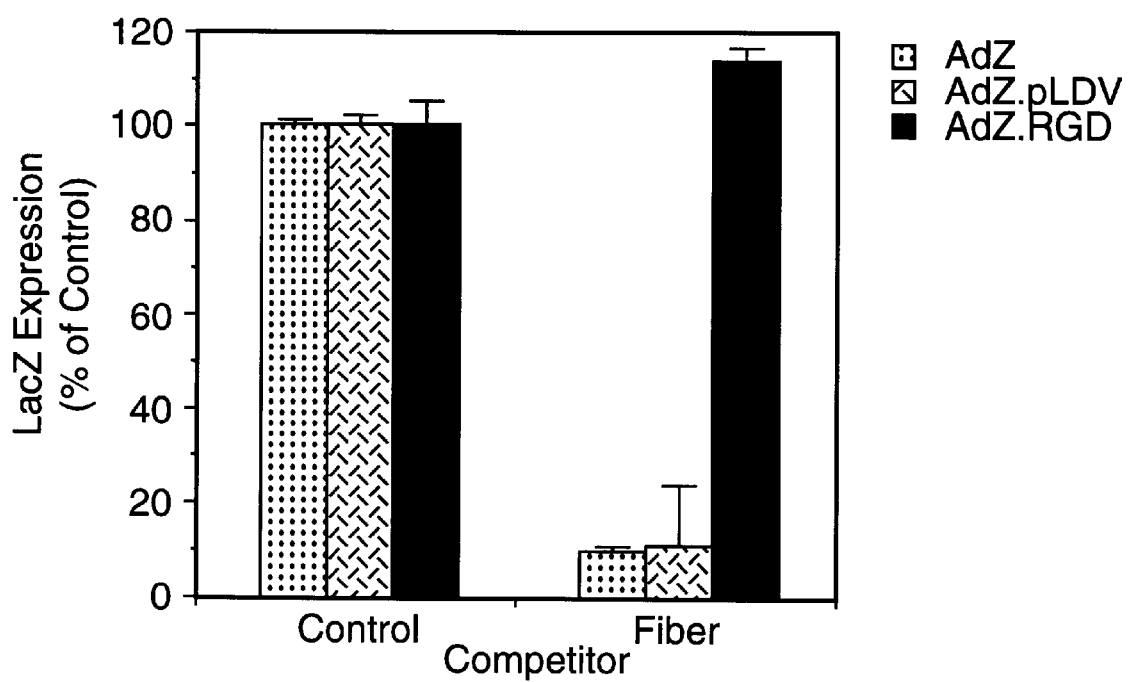
FIG. 20 is a bar graph depicting β-galactosidase expression (% of control) in 293 cells transduced with either ADZ.RGD (closed bars), AdZ.pRGD (stippled bars), or AdZ (open bars) in the absence (control) or presence (fiber) of soluble fiber protein.

The ability of the RGD motif to effect cell targeting similarly was studied in αv-integrins expressing 293 cells. These studies were carried out as for the other peptide motifs/cell lines. However, for comparative purposes, the vectors AdZ and AdZ.pRGD (i.e., the vector containing multiple copies of the RGD motif not having cysteine residues) were also included. The results of these studies are presented in FIG. 20. As can be seen from this figure, AdZ.RGD, but not AdZ.pRGD, clearly was able to overcome the fiber-mediated block to adenoviral-mediated gene delivery.

These results thus confirm that the RGD peptide motif (i.e., present as a loop at the C-terminus of the fiber protein), like the RKKK2 motif present in a loop of the adenovirus fiber protein (described in Example 4), is of sufficiently high affinity that it was able to overcome the fiber-mediated block to adenoviral-mediated gene delivery, and effectively "swamp out" the typical interaction of wild-type fiber protein with its cellular receptor to target the adenovirus to a new receptor.

The results further confirm that the constraint of a non-native amino acid sequence (i.e., either through insertion in a fiber loop or creation of a loop like structure at the fiber terminus) can result in the creation of a high affinity peptide motif. Such a high affinity peptide motif is of use in adenoviral cell targeting.

All of the references cited herein, including patents, patent applications, and publications, are hereby incorporated in their entireties by reference to the same extent as if each reference were set forth in its entirety herein.

While this invention has been described with an emphasis upon preferred embodiments, it will be apparent to those of ordinary skill in the art that variations in the preferred embodiments can be prepared and used and that the invention can be practiced otherwise than as specifically described herein. The present invention is intended to include such variations and alternative practices. Accordingly, this invention includes all modifications encompassed within the spirit and scope of the invention as defined by the following claims.

What is claimed is:

1. A chimeric adenovirus fiber protein comprising a nonnative amino acid sequence that is constrained by a preexisting adenoviral fiber knob loop.

2. The chimeric adenovirus fiber protein of claim 1, which directs entry into cells of a vector comprising said chimeric adenovirus fiber protein that is more efficient than entry into cells of a vector that is identical except for comprising a wild-type adenovirus fiber protein rather than said chimeric adenovirus protein.

3. The chimeric adenovirus fiber protein of claim 1, which binds a binding site present on a cell surface which wild-type fiber protein does not bind.

4. The chimeric adenovirus fiber protein of claim 1, wherein said nonnative amino acid sequence comprises an epitope for an antibody or a ligand for a cell surface binding site.

5. The chimeric adenovirus fiber protein of claim 1, wherein said nonnative amino acid sequence comprises from about 3 to about 200 amino acids.

6. The chimeric adenovirus fiber protein of claim 1, wherein said nonnative amino acid sequence comprises from about 3 to about 30 amino acids.

7. The chimeric adenovirus fiber protein of claim 1, wherein said nonnative amino acid sequence comprises an RGD sequence.

8. The chimeric adenovirus fiber protein of claim 1, wherein said nonnative amino acid sequence comprises a sequence selected from the group consisting of SEQ ID NO:1, SEQ ID NO:2, SEQ ID NO:3, SEQ ID NO:4, SEQ ID NO:5, SEQ ID NO:17, SEQ ID NO:19, SEQ ID NO:23, SEQ ID NO:31, SEQ ID NO:35, SEQ ID NO:39, SEQ ID NO:43, SEQ ID NO:49, SEQ ID NO:53, SEQ ID NO:56, SEQ ID NO:59, SEQ ID NO:63, SEQ ID NO:66, SEQ ID NO:67, SEQ ID NO:68, and SEQ ID NO:79, and wherein said sequence may be deleted at either the C- or N-terminus by 1, 2, or 3 residues.

9. The chimeric adenovirus fiber protein of claim 8, wherein said nonnative amino acid sequence is selected from the group consisting of SEQ ID NO:3, SEQ ID NO:4, and SEQ ID NO:5.

10. The chimeric adenovirus fiber protein of claim 1, wherein said nonnative amino acid sequence comprises a sequence selected from the group consisting of SEQ ID NO:1, SEQ ID NO:2, SEQ ID NO:3, SEQ ID NO:4, SEQ ID NO:5, SEQ ID NO:17, SEQ ID NO:19, SEQ ID NO:23, SEQ ID NO:31, SEQ ID NO:35, SEQ ID NO:39, SEQ ID NO:43, SEQ ID NO:49, SEQ ID NO:53, SEQ ID NO:56, SEQ ID NO:59, SEQ ID NO:63, SEQ ID NO:66, SEQ ID NO:67, SEQ ID NO:68, and SEQ ID NO:79, and conservative amino acid substitutions thereof.

11. The chimeric adenovirus fiber protein of claim 10, wherein said nonnative amino acid sequence is selected from the group consisting of SEQ ID NO:3, SEQ ID NO:4, and SEQ ID NO:5.

12. An adenovirus comprising the chimeric adenovirus fiber protein of claim 1.

13. The adenovirus of claim 12, further comprising a genome comprising a passenger gene.

14. A host cell comprising the adenovirus of claim 12.

15. A nucleic acid encoding the protein of claim 1.

16. A vector comprising the nucleic acid of claim 15.

17. The vector of claim 16, wherein said vector is a viral vector.

18. The vector of claim 16, wherein said vector is an adenoviral vector.

19. The vector of claim 16, wherein said vector further comprises a passenger gene.

20. A host cell comprising the vector of claim 16.

* * * * *

SEQUENCE LISTING (1) GENERAL INFORMATION:

(iii) NUMBER OF SEQUENCES: 80

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Arg Lys Lys Lys Arg Lys Lys Lys
1               5

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asp Tyr Lys Asp Asp Asp Asp Lys
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Cys Asp Cys Arg Gly Asp Cys Phe Cys
1               5

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Cys Xaa Cys Arg Gly Asp Cys Xaa Cys
1               5

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Cys Xaa Xaa Xaa Xaa Xaa Xaa Xaa Xaa Cys Arg Gly Asp Cys Xaa Xaa
1               5                   10                  15

Xaa Xaa Xaa Xaa Xaa Xaa Cys
            20

(2) INFORMATION FOR SEQ ID NO:6:

(i) SEQUENCE CHARACTERISTICS:
          (A) LENGTH: 22 base pairs
          (B) TYPE: nucleic acid
          (C) STRANDEDNESS: double
          (D) TOPOLOGY: linear (ii) MOLECULE TYPE: DNA (genomic)

(xi) SEQUENCE DESCRIPTION: SEQ ID NO:6:

TCA TAC ATT GCC CAA GAA TAA A                                       22
Ser Tyr Ile Ala Gln Glu
 1           5

(2) INFORMATION FOR SEQ ID NO:7:

(i) SEQUENCE CHARACTERISTICS:
          (A) LENGTH: 6 amino acids
          (B) TYPE: amino acid
          (D) TOPOLOGY: linear (ii) MOLECULE TYPE: peptide (xi) SEQUENCE DESCRIPTION: SEQ ID NO:7:

Ser Tyr Ile Ala Gln Glu
 1           5

(2) INFORMATION FOR SEQ ID NO:8:

(i) SEQUENCE CHARACTERISTICS:
          (A) LENGTH: 30 base pairs
          (B) TYPE: nucleic acid
          (C) STRANDEDNESS: double
          (D) TOPOLOGY: linear (ii) MOLECULE TYPE:  DNA (genomic)

(xi) SEQUENCE DESCRIPTION: SEQ ID NO:8:

TCA TAC ATT GCC CAA GAA GGA TCC AAT AAA                             30
Ser Tyr Ile Ala Gln Glu Gly Ser Asn Lys
         10                  15

(2) INFORMATION FOR SEQ ID NO:9:

(i) SEQUENCE CHARACTERISTICS:
          (A) LENGTH: 10 amino acids
          (B) TYPE: amino acid
          (D) TOPOLOGY: linear (ii) MOLECULE TYPE: peptide (xi) SEQUENCE DESCRIPTION: SEQ ID NO:9:

Ser Tyr Ile Ala Gln Glu Gly Ser Asn Lys
 1           5                   10

(2) INFORMATION FOR SEQ ID NO:10:

(i) SEQUENCE CHARACTERISTICS:

(A) LENGTH: 43 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

TCCCCCCGGG TCTAGATTAG GATCCTTCTT GGGCAATGTA TGA          43

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

CGTGTATCCA TATGACACAG A                                  21

(2) INFORMATION FOR SEQ ID NO:12:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

TATGGAGGAT CCAATAAAGA ATCGTTTGTG TTATGTTTCA ACGTGTTTAT TTTTC          55

(2) INFORMATION FOR SEQ ID NO:13:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

AATTGAAAAA TAAACACGTT GAAACATAAC ACAAACGATT CTTTATTGGA TCCTCCA          57

(2) INFORMATION FOR SEQ ID NO:14:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

GGCCATGGCC TAGAATTTGA TTCAAACGGT GCCATGATTA CTAAACTTGG AGCG          54

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

GCGGATCCTT ATTCCTGGGC AATGTAGGA                                    29

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

ATT ACA CTT AAT GGC ACT AGT GAA TCC ACA GAA ACT                   36
Ile Thr Leu Asn Gly Thr Ser Glu Ser Thr Glu Thr
              15                  20

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:17:

Ile Thr Leu Asn Gly Thr Ser Glu Ser Thr Glu Thr
 1            5               10

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

ACT AGA AAA AAA AAA CGC AAG AAG AAG ACT AGT                       33
Thr Arg Lys Lys Lys Arg Lys Lys Lys Thr Ser
              15              20

(2) INFORMATION FOR SEQ ID NO:19:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:19:

Thr Arg Lys Lys Lys Arg Lys Lys Lys Thr Ser
 1            5               10

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:20:

CTAGAAAGAA GAAACGCAAA AAGAAGA                                        27

(2) INFORMATION FOR SEQ ID NO:21:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:21:

CTAGTCTTCT TTTTGCGTTT CTTCTTT                                        27

(2) INFORMATION FOR SEQ ID NO:22:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:22:

ACT AGA GAC TAC AAG GAC GAC GAT GAT AAG ACT AGT                      36
Thr Arg Asp Tyr Lys Asp Asp Asp Asp Lys Thr Ser
            15                  20

(2) INFORMATION FOR SEQ ID NO:23:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:23:

Thr Arg Asp Tyr Lys Asp Asp Asp Asp Lys Thr Ser
 1               5                  10

(2) INFORMATION FOR SEQ ID NO:24:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:24:

CTAGAGACTA CAAGGACGAC GATGATAAGA                                     30

(2) INFORMATION FOR SEQ ID NO:25:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:25:

```
CTAGTCTTAT CATCGTCGTC CTTGTAGTCT                                30
```

(2) INFORMATION FOR SEQ ID NO:26:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

```
ATT ACA CTT AAT GGC ACT AGA AAG AAG AAA CGC AAA AAG AAG ACT AGT    48
Ile Thr Leu Asn Gly Thr Arg Lys Lys Lys Arg Lys Lys Lys Thr Ser
            15                  20                  25

GAA TCC ACA GAA ACT                                                63
Glu Ser Thr Glu Thr
        30
```

(2) INFORMATION FOR SEQ ID NO:27:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:27:

```
Ile Thr Leu Asn Gly Thr Arg Lys Lys Lys Arg Lys Lys Lys Thr Ser
  1               5                  10                  15

Glu Ser Thr Glu Thr
            20
```

(2) INFORMATION FOR SEQ ID NO:28:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:28:

```
ATT ACA CTT AAT GGC ACT AGA GAC TAC AAG GAC GAC GAT GAT AAG ACT    48
Ile Thr Leu Asn Gly Thr Arg Asp Tyr Lys Asp Asp Asp Asp Lys Thr
            25                  30                  35

AGT GAA TCC ACA GAA ACT                                            66
Ser Glu Ser Thr Glu Thr
        40
```

(2) INFORMATION FOR SEQ ID NO:29:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:29:

```
Ile Thr Leu Asn Gly Thr Arg Asp Tyr Lys Asp Asp Asp Asp Lys Thr
  1               5                  10                  15
```

```
Ser Glu Ser Thr Glu Thr
            20
```

(2) INFORMATION FOR SEQ ID NO:30:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:30:

```
ACT AGA GCC TGC GAC TGT CGC GGC GAT TGT TTT TGC GGT ACT AGT        45
Thr Arg Ala Cys Asp Cys Arg Gly Asp Cys Phe Cys Gly Thr Ser
            25                  30                  35
```

(2) INFORMATION FOR SEQ ID NO:31:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:31:

```
Thr Arg Ala Cys Asp Cys Arg Gly Asp Cys Phe Cys Gly Thr Ser
 1               5                  10                  15
```

(2) INFORMATION FOR SEQ ID NO:32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:32:

```
CTAGAGCCTG CGACTGTCGC GGCGATTGTT TTTGCGGTA                         39
```

(2) INFORMATION FOR SEQ ID NO:33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:33:

```
CTAGTACCGC AAAAACAATC GCCGCGACAG TCGCAGGCT                         39
```

(2) INFORMATION FOR SEQ ID NO:34:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:34:

```
ACT AGA TGC CGC CGC GAA ACC GCT TGG GCC TGT ACT AGT        39
Thr Arg Cys Arg Arg Glu Thr Ala Trp Ala Cys Thr Ser
            20                  25
```

(2) INFORMATION FOR SEQ ID NO:35:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:35:

```
Thr Arg Cys Arg Arg Glu Thr Ala Trp Ala Cys Thr Ser
 1           5                  10
```

(2) INFORMATION FOR SEQ ID NO:36:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:36:

```
CTAGATGCCG CCGCGAAACC GCTTGGGCCT GTA                        33
```

(2) INFORMATION FOR SEQ ID NO:37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:37:

```
CTAGTACAGG CCCAAGCGGT TTCGCGGCGG CAT                        33
```

(2) INFORMATION FOR SEQ ID NO:38:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:38:

```
ACT AGA GAC ATT ACC TGG GAC CAG CTT TGG GAC CTT ATG AAG ACT AGT    48
Thr Arg Asp Ile Thr Trp Asp Gln Leu Trp Asp Leu Met Lys Thr Ser
        15                  20                  25
```

(2) INFORMATION FOR SEQ ID NO:39:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:39:

Thr Arg Asp Ile Thr Trp Asp Gln Leu Trp Asp Leu Met Lys Thr Ser (2) INFORMATION FOR SEQ ID NO:40:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:40:

CTAGAGACAT TACCTGGGAC CAGCTTTGGG ACCTTATGAA GA          42

(2) INFORMATION FOR SEQ ID NO:41:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:41:

CTAGTCTTCA TAAGGTCCCA AAGCTGGTCC CAGGTAATGT CT          42

(2) INFORMATION FOR SEQ ID NO:42:

(i) SEQUENCE CHARACTERISTICS:
        (A) LENGTH: 45 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:42:

ACT AGA AAG AAG AAG CGC AAA AAA AAA AGA AAG AAG AAG ACT AGT          45
Thr Arg Lys Lys Lys Arg Lys Lys Lys Arg Lys Lys Lys Thr Ser
 15               20               25

(2) INFORMATION FOR SEQ ID NO:43:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:43:

Thr Arg Lys Lys Lys Arg Lys Lys Lys Arg Lys Lys Lys Thr Ser
 1            5              10            15

(2) INFORMATION FOR SEQ ID NO:44:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:44:

CTAGAAAGAA GAAGCGCAAA AAAAAAGAA AGAAGAAGA          39

(2) INFORMATION FOR SEQ ID NO:45:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:45:

```
CTAGTCTTCT TCTTTCTTTT TTTTTTGCGC TTCTTCTTT                          39
```

(2) INFORMATION FOR SEQ ID NO:46:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:46:

```
GATCAGGATC AGGTTCAGGG AGTGGCTCTG CCTGCGACTG TCGCGGCGAT TGTTTTTGCG    60

GTTAAG                                                               66
```

(2) INFORMATION FOR SEQ ID NO:47:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:47:

```
GATCCTTAAC CGCAAAAACA ATCGCCGCGA CAGTCGCAGG CAGAGCCACT CCCTGAACCT    60

GATCCT                                                               66
```

(2) INFORMATION FOR SEQ ID NO:48:

(i) SEQUENCE CHARACTERISTICS:
        (A) LENGTH: 86 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:48:

```
GCC CAA GAA GGA TCA GGA TCA GGT TCA GGG AGT GGC TCT GCC TGC GAC      48
Ala Gln Glu Gly Ser Gly Ser Gly Ser Gly Ser Gly Ser Ala Cys Asp
            20                  25                  30

TGT CGC GGC GAT TGT TTT TGC GGT TAA GGA TCC AAT  AA                  86
Cys Arg Gly Asp Cys Phe Cys Gly
                35                  40
```

(2) INFORMATION FOR SEQ ID NO:49:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:49:

```
Ala Gln Glu Gly Ser Gly Ser Gly Ser Gly Ser Ala Cys Asp
 1               5                  10                  15

Cys Arg Gly Asp Cys Phe Cys Gly
                20
```

(2) INFORMATION FOR SEQ ID NO:50:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:50:

```
GATCCGGTTC AGGATCTGGC AGTGGCTCGA CTAGTTAAA                      39
```

(2) INFORMATION FOR SEQ ID NO:51:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:51:

```
GATCTTTAAC TAGTCGAGCC ACTGCCAGAT CCTGAACCG                      39
```

(2) INFORMATION FOR SEQ ID NO:52:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:52:

```
ACT AGT GGA AGA GGA GAT ACT TTT GGC CGC GGC GAC ACG TTC GGA AGG     48
Thr Ser Gly Arg Gly Asp Thr Phe Gly Arg Gly Asp Thr Phe Gly Arg
     30                  35                  40

GGG GAT ACA TTT TCT AGT                                             66
Gly Asp Thr Phe Ser Ser
 45                  50
```

(2) INFORMATION FOR SEQ ID NO:53:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:53:

```
Thr Ser Gly Arg Gly Asp Thr Phe Gly Arg Gly Asp Thr Phe Gly Arg
 1               5                  10                  15

Gly Asp Thr Phe Ser Ser
                20
```

(2) INFORMATION FOR SEQ ID NO:54:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:54:

```
CTAGTGGAAG AGGAGATACT TTTGGCCGCG GCGACACGTT CGGAAGGGGG GATACATTTT      60
```

(2) INFORMATION FOR SEQ ID NO:55:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:55:

```
CTAGAAAATG TATCCCCCCT TCCGAACGTG TCGCCGCGGC CAAAAGTATC TCCTCTTCCA      60
```

(2) INFORMATION FOR SEQ ID NO:56:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:56:

```
Glu Ile Leu Asp Val Pro Ser Thr
1               5
```

(2) INFORMATION FOR SEQ ID NO:57:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

```
Glu Ile Leu Asp Val Pro Ser Glu Ile Leu Asp Val Pro Ser Glu Ile
1               5                   10                  15
Leu Asp Val Pro Ser
            20
```

(2) INFORMATION FOR SEQ ID NO:58:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:58:

```
ACT AGT GAA ATT CTT GAC GTC GGA GAG ATC CTC GAC GTC GGG GAA ATA      48
Thr Ser Glu Ile Leu Asp Val Gly Glu Ile Leu Asp Val Gly Glu Ile
```

```
                25                  30                  35
CTG GAC GTC TCT AGT                                                      63
Leu Asp Val Ser Ser
        40
```

(2) INFORMATION FOR SEQ ID NO:59:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:59:

```
Thr Ser Glu Ile Leu Asp Val Gly Glu Ile Leu Asp Val Gly Glu Ile
 1               5                  10                  15

Leu Asp Val Ser Ser
        20
```

(2) INFORMATION FOR SEQ ID NO:60:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:60:

```
CTAGTGAAAT TCTTGACGTC GGAGAGATCC TCGACGTCGG GGAAATACTG GACGTCT          57
```

(2) INFORMATION FOR SEQ ID NO:61:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:61:

```
CTAGAGACGT CCAGTATTTC CCCGACGTCG AGGATCTCTC CGACGTCAAG AATTTCA          57
```

(2) INFORMATION FOR SEQ ID NO:62:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:62:

```
ACT AGT GGA TAC ATC GGC AGT CGC GGT TAC ATT GGG TCC CGA GGA TAT          48
Thr Ser Gly Tyr Ile Gly Ser Arg Gly Tyr Ile Gly Ser Arg Gly Tyr
                25                  30                  35

ATA GGC TCA AGA TCT AGT                                                  66
Ile Gly Ser Arg Ser Ser
        40
```

(2) INFORMATION FOR SEQ ID NO:63:

(i) SEQUENCE CHARACTERISTICS:

(A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:63:

Thr Ser Gly Tyr Ile Gly Ser Arg Gly Tyr Ile Gly Ser Arg Gly Tyr
1               5                   10                  15
Ile Gly Ser Arg Ser Ser
            20

(2) INFORMATION FOR SEQ ID NO:64:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:64:

CTAGTGGATA CATCGGCAGT CGCGGTTACA TTGGGTCCCG AGGATATATA GGCTCAAGAT      60

(2) INFORMATION FOR SEQ ID NO:65:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:65:

CTAGATCTTG AGCCTATATA TCCTCGGGAC CCAATGTAAC CGCGACTGCC GATGTATCCA      60

(2) INFORMATION FOR SEQ ID NO:66:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Tyr Ile Gly Ser Arg
1               5

(2) INFORMATION FOR SEQ ID NO:67:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Tyr Ile Gly Ser Arg Gly
1               5

(2) INFORMATION FOR SEQ ID NO:68:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:68:

Ser Ala Cys Asp Cys Arg Gly Asp Cys Phe Cys Cys Thr Ser
1               5                   10

(2) INFORMATION FOR SEQ ID NO:69:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:69:

Ile Thr Leu Asn Gly
1               5

(2) INFORMATION FOR SEQ ID NO:70:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:70:

Glu Ser Thr Glu Thr
1               5

(2) INFORMATION FOR SEQ ID NO:71:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:71:

Phe Ser Tyr Ile Ala Gln Glu
1               5

(2) INFORMATION FOR SEQ ID NO:72:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:72:

Gly Ser Gly Ser Gly Ser Gly Ser Gly Ser
1               5                   10

(2) INFORMATION FOR SEQ ID NO:73:

(i) SEQUENCE CHARACTERISTICS:
    (A) LENGTH: 36 base pairs
    (B) TYPE: nucleic acid
    (C) STRANDEDNESS: double
    (D) TOPOLOGY: linear (ii) MOLECULE TYPE: other nucleic acid (xi) SEQUENCE DESCRIPTION: SEQ ID NO:73:

```
ATT ACA CTT AAT GGC ACT AGT GAA TCC ACA GAA ACT            36
Ile Thr Leu Asn Gly Thr Ser Glu Ser Thr Glu Thr
        25                  30
```

(2) INFORMATION FOR SEQ ID NO:74:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:74:

```
Ile Thr Leu Asn Gly Thr Ser Glu Ser Thr Glu Thr
 1               5                  10
```

(2) INFORMATION FOR SEQ ID NO:75:

(i) SEQUENCE CHARACTERISTICS:
        (A) LENGTH: 105 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:75:

```
GCC CAA GAA GGA TCC GGT TCA GGA TCT GGC AGT GGC TCG ACT AGT GAA    48
Ala Gln Glu Gly Ser Gly Ser Gly Ser Gly Ser Gly Ser Thr Ser Glu
        30                  35                  40

ATT CTT GAC GTC GGA GAG ATC CTC GAC GTC GGG GAA ATA CTG GAC GTC    96
Ile Leu Asp Val Gly Glu Ile Leu Asp Val Gly Glu Ile Leu Asp Val
 45                  50                  55                  60

TCT AGT TAA                                                       105
Ser Ser
```

(2) INFORMATION FOR SEQ ID NO:76:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:76:

```
Ala Gln Glu Gly Ser Gly Ser Gly Ser Gly Ser Gly Ser Thr Ser Glu
 1               5                  10                  15

Ile Leu Asp Val Gly Glu Ile Leu Asp Val Gly Glu Ile Leu Asp Val
            20                  25                  30

Ser Ser
```

(2) INFORMATION FOR SEQ ID NO:77:

(i) SEQUENCE CHARACTERISTICS:
        (A) LENGTH: 108 base pairs

```
            (B) TYPE: nucleic acid
            (C) STRANDEDNESS: double
            (D) TOPOLOGY: linear (ii) MOLECULE TYPE: other nucleic acid (xi) SEQUENCE DESCRIPTION: SEQ ID NO:77:

GCC CAA GAA GGA TCC GGT TCA GGA TCT GGC AGT GGC TCG ACT AGT GGA      48
Ala Gln Glu Gly Ser Gly Ser Gly Ser Gly Ser Gly Ser Thr Ser Gly
                 40                  45                  50

TAC ATC GGC AGT CGC GGT TAC ATT GGG TCC CGA GGA TAT ATA GGC TCA      96
Tyr Ile Gly Ser Arg Gly Tyr Ile Gly Ser Arg Gly Tyr Ile Gly Ser
             55                  60                  65

AGA TCT AGT TAA                                                     108
Arg Ser Ser
         70

(2) INFORMATION FOR SEQ ID NO:78:

(i) SEQUENCE CHARACTERISTICS:
            (A) LENGTH: 35 amino acids
            (B) TYPE: amino acid
            (D) TOPOLOGY: linear (ii) MOLECULE TYPE: peptide (xi) SEQUENCE DESCRIPTION: SEQ ID NO:78:

Ala Gln Glu Gly Ser Gly Ser Gly Ser Gly Ser Gly Ser Thr Ser Gly
 1               5                  10                  15

Tyr Ile Gly Ser Arg Gly Tyr Ile Gly Ser Arg Gly Tyr Ile Gly Ser
             20                  25                  30

Arg Ser Ser
         35

(2) INFORMATION FOR SEQ ID NO:79:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:79:

Ser Ala Cys Asp Cys Arg Gly Asp Cys Phe Cys Gly
 1               5                  10

(2) INFORMATION FOR SEQ ID NO:80:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:80:

Glu Ile Leu Asp Val Pro Ser
 1               5
```